United States Patent [19]
Cosman

[11] Patent Number: 6,006,126
[45] Date of Patent: *Dec. 21, 1999

[54] SYSTEM AND METHOD FOR STEREOTACTIC REGISTRATION OF IMAGE SCAN DATA

[76] Inventor: Eric R. Cosman, 872 Concord Ave., Belmont, Mass. 02178

[ * ] Notice: This patent is subject to a terminal disclaimer.

[21] Appl. No.: 08/475,681

[22] Filed: Jun. 7, 1995

Related U.S. Application Data

[63] Continuation-in-part of application No. 08/441,788, May 16, 1995, which is a continuation of application No. 08/299,987, Sep. 1, 1994, abandoned, which is a continuation of application No. 08/047,879, Apr. 15, 1993, abandoned, which is a continuation of application No. 07/941,863, Sep. 8, 1992, abandoned, which is a continuation of application No. 07/647,463, Jan. 28, 1991, abandoned.

[51] Int. Cl.$^6$ .................................................. A61B 05/00
[52] U.S. Cl. ..................... 600/426; 600/414; 600/417; 600/429; 606/130
[58] Field of Search ................................ 128/665, 653.1, 128/920, 922; 606/130; 378/205, 206; 356/247; 600/407, 410, 414, 415, 417, 473, 476; 348/77, 164

[56] References Cited

U.S. PATENT DOCUMENTS

| | | |
|---|---|---|
| 3,821,469 | 6/1974 | Whetstone et al. . |
| 3,983,474 | 9/1976 | Kuipers . |
| 4,058,114 | 11/1977 | Soldner . |
| 4,068,156 | 1/1978 | Johnson et al. . |
| 4,068,556 | 1/1978 | Foley . |
| 4,182,312 | 1/1980 | Mushabac . |
| 4,262,306 | 4/1981 | Renner . |
| 4,341,220 | 7/1982 | Perry . |
| 4,358,856 | 11/1982 | Stivender et al. . |
| 4,407,298 | 10/1983 | Lentz et al. . |
| 4,457,311 | 7/1984 | Sorenson et al. . |
| 4,465,069 | 8/1984 | Barbier et al. . |
| 4,473,074 | 9/1984 | Vassiliadis . |
| 4,506,676 | 3/1985 | Duska . |

(List continued on next page.)

FOREIGN PATENT DOCUMENTS

| | | |
|---|---|---|
| 0629963A2 A3 | 12/1994 | European Pat. Off. . |
| WO 94/23647 | 10/1994 | WIPO . |
| WO 95/25475 | 9/1995 | WIPO . |

OTHER PUBLICATIONS

S. Lavallee et al., "Computer Assisted Puncture", AFCET INRIA 1:439–49, Nov. 1987.

*Primary Examiner*—Jeffrey R. Jastrzab
*Assistant Examiner*—Shawna J Shaw
*Attorney, Agent, or Firm*—Darby & Darby P.C.

[57] ABSTRACT

A system for computer graphic determination and display of a patient's anatomy, as from CT or MR scanning, and stored along with associated equipment in an object field including the patient's anatomy. A first digitizing camera structure produces a signal representative of its field-of-view which defines coordinates of index points in its field-of-view. A second digitizing camera structure produces similar output for an offset field-of-view. The two camera positions are defined with respect to the patient's anatomy so that the fields-of-view of the cameras include both the patient's anatomy and the equipment, but are taken from different directions. Index markers are for fixing points in the fields of view and accordingly locate equipment relative to said patient anatomy. The index markers are provided by variety of structures including, light sources in various forms as reflectors, diodes, and laser scanner structures to provide a visible grid, mesh or cloud of points.

79 Claims, 12 Drawing Sheets

U.S. PATENT DOCUMENTS

| | | |
|---|---|---|
| 4,535,782 | 8/1985 | Zoltan . |
| 4,571,834 | 2/1986 | Fraser et al. . |
| 4,583,538 | 4/1986 | Onik et al. . |
| 4,592,352 | 6/1986 | Patil . |
| 4,598,368 | 7/1986 | Umemura . |
| 4,602,622 | 7/1986 | Bär et al. . |
| 4,608,977 | 9/1986 | Brown . |
| 4,618,978 | 10/1986 | Cosman . |
| 4,638,798 | 1/1987 | Shelden et al. . |
| 4,645,343 | 2/1987 | Stockdale et al. . |
| 4,651,732 | 3/1987 | Frederick . |
| 4,659,971 | 4/1987 | Suzuki et al. . |
| 4,660,970 | 4/1987 | Ferrano . |
| 4,674,057 | 6/1987 | Caughman et al. . |
| 4,686,997 | 8/1987 | Oloff et al. . |
| 4,698,777 | 10/1987 | Toyoda et al. . |
| 4,701,049 | 10/1987 | Beckmann et al. . |
| 4,701,407 | 10/1987 | Appel . |
| 4,705,395 | 11/1987 | Hageniers . |
| 4,705,401 | 11/1987 | Addleman et al. . |
| 4,706,665 | 11/1987 | Gouda . |
| 4,709,156 | 11/1987 | Murphy et al. . |
| 4,722,056 | 1/1988 | Roberts et al. . |
| 4,723,544 | 2/1988 | Moore et al. . |
| 4,733,661 | 3/1988 | Palestrant . |
| 4,733,969 | 3/1988 | Case et al. . |
| 4,737,032 | 4/1988 | Addleman et al. . |
| 4,742,815 | 5/1988 | Ninan et al. . |
| 4,743,770 | 5/1988 | Lee . |
| 4,743,771 | 5/1988 | Sacks et al. . |
| 4,745,290 | 5/1988 | Frankel et al. . |
| 4,750,487 | 6/1988 | Zanetti . |
| 4,753,128 | 6/1988 | Barlett et al. . |
| 4,753,528 | 6/1988 | Hines et al. . |
| 4,761,072 | 8/1988 | Pryor . |
| 4,762,016 | 8/1988 | Stoughton et al. . |
| 4,764,016 | 8/1988 | Johanasson . |
| 4,776,749 | 10/1988 | Wanzenberg et al. . |
| 4,779,212 | 10/1988 | Levy . |
| 4,791,934 | 12/1988 | Brunnett . |
| 4,794,262 | 12/1988 | Sato et al. . |
| 4,797,736 | 1/1989 | Kloots et al. . |
| 4,805,615 | 2/1989 | Carol . |
| 4,809,694 | 3/1989 | Ferrara . |
| 4,821,200 | 4/1989 | Oberg . |
| 4,821,206 | 4/1989 | Arora . |
| 4,822,163 | 4/1989 | Schmidt . |
| 4,825,091 | 4/1989 | Breyer et al. . |
| 4,829,373 | 5/1989 | Leberl et al. . |
| 4,835,710 | 5/1989 | Schnelle et al. . |
| 4,836,778 | 6/1989 | Baumrind et al. . |
| 4,838,265 | 6/1989 | Cosman et al. . |
| 4,841,967 | 6/1989 | Chang et al. . |
| 4,859,181 | 8/1989 | Neumeyer . |
| 4,869,247 | 9/1989 | Howard, III et al. . |
| 4,875,478 | 10/1989 | Chen . |
| 4,896,673 | 1/1990 | Rose et al. . |
| 4,931,056 | 6/1990 | Ghajar et al. . |
| 4,933,843 | 6/1990 | Scheller et al. . |
| 4,943,296 | 7/1990 | Funakubo et al. . |
| 4,945,914 | 8/1990 | Allen . |
| 4,954,043 | 9/1990 | Yoshida et al. . |
| 4,955,891 | 9/1990 | Carol . |
| 4,961,422 | 10/1990 | Marchosky et al. . |
| 4,991,579 | 2/1991 | Allen . |
| 5,016,639 | 5/1991 | Allen . |
| 5,017,139 | 5/1991 | Mushabac . |
| 5,027,818 | 7/1991 | Bova et al. . |
| 5,047,036 | 9/1991 | Koutrouvelis . |
| 5,050,608 | 9/1991 | Watanabe et al. . |
| 5,070,454 | 12/1991 | Griffith . |
| 5,078,140 | 1/1992 | Kwoh . |
| 5,080,662 | 1/1992 | Paul . |
| 5,086,401 | 2/1992 | Glassman et al. . |
| 5,094,241 | 3/1992 | Allen . |
| 5,097,839 | 3/1992 | Allen . |
| 5,099,846 | 3/1992 | Hardy . |
| 5,107,839 | 4/1992 | Houdek et al. . |
| 5,116,344 | 5/1992 | Sundqviat . |
| 5,119,817 | 6/1992 | Allen . |
| 5,142,559 | 8/1992 | Wielopolski et al. . |
| 5,142,930 | 9/1992 | Allen et al. . |
| 5,186,174 | 2/1993 | Schlöndorff et al. . |
| 5,193,106 | 3/1993 | DeSena . |
| 5,197,476 | 3/1993 | Nowacki et al. . |
| 5,198,977 | 3/1993 | Salb . |
| 5,207,223 | 5/1993 | Adler . |
| 5,211,164 | 5/1993 | Allen . |
| 5,222,499 | 6/1993 | Allen et al. . |
| 5,224,049 | 6/1993 | Mushabac . |
| 5,230,338 | 7/1993 | Allen et al. . |
| 5,230,623 | 7/1993 | Guthrie et al. . |
| 5,233,990 | 8/1993 | Barnes . |
| 5,251,127 | 10/1993 | Raab . |
| 5,257,998 | 11/1993 | Ota et al. . |
| 5,260,871 | 11/1993 | Goldberg . |
| 5,285,772 | 2/1994 | Rattner . |
| 5,295,483 | 3/1994 | Nowacki et al. . |
| 5,305,203 | 4/1994 | Raab . |
| 5,307,807 | 5/1994 | Valdès Sosa et al. . |
| 5,309,913 | 5/1994 | Kormos et al. . |
| 5,315,630 | 5/1994 | Sturm et al. . |
| 5,354,314 | 10/1994 | Hardy et al. . |
| 5,383,454 | 1/1995 | Bucholz . |
| 5,389,101 | 2/1995 | Heilbrun et al. . |
| 5,397,329 | 3/1995 | Allen . |
| 5,398,684 | 3/1995 | Hardy ............................... 128/653.1 |
| 5,446,548 | 8/1995 | Gerig et al. . |
| 5,588,430 | 12/1996 | Bova et al. .......................... 128/653.1 |
| 5,617,857 | 4/1997 | Chader . |
| 5,622,170 | 4/1997 | Schulz . |
| 5,622,187 | 4/1997 | Carol ..................................... 128/897 |
| 5,662,111 | 9/1997 | Cosman . |
| 5,682,890 | 11/1997 | Kormos et al. . |
| 5,755,725 | 5/1998 | Drusis . |
| 5,776,064 | 7/1998 | Kalfae et al. . |
| 5,792,146 | 8/1998 | Cosman . |
| 5,792,147 | 8/1998 | Evans et al. . |
| 5,836,954 | 11/1998 | Hellbrun et al. . |
| 5,848,967 | 12/1998 | Cosman . |

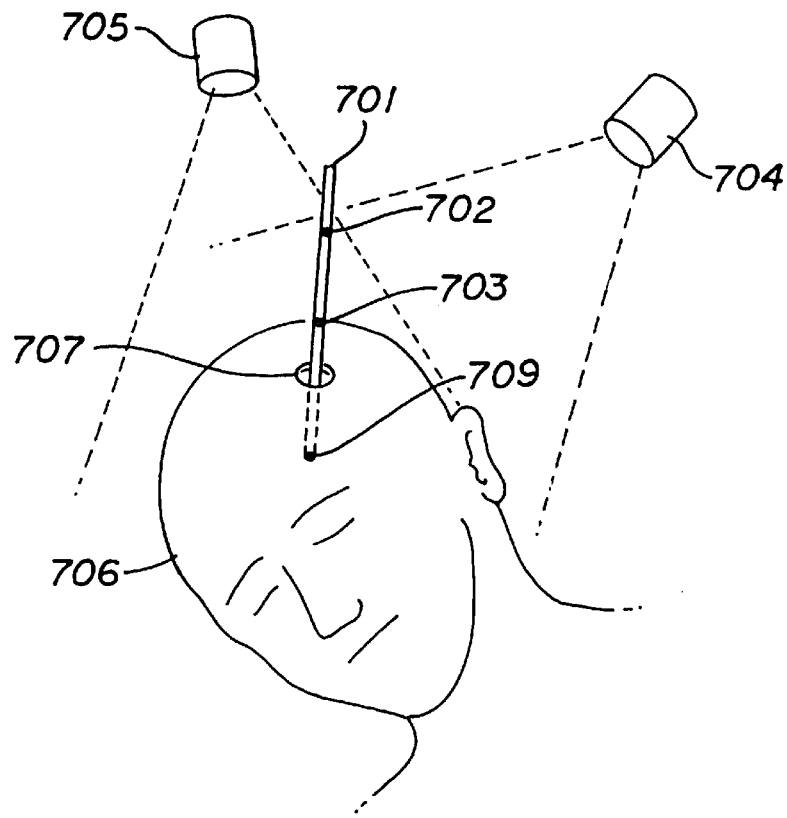
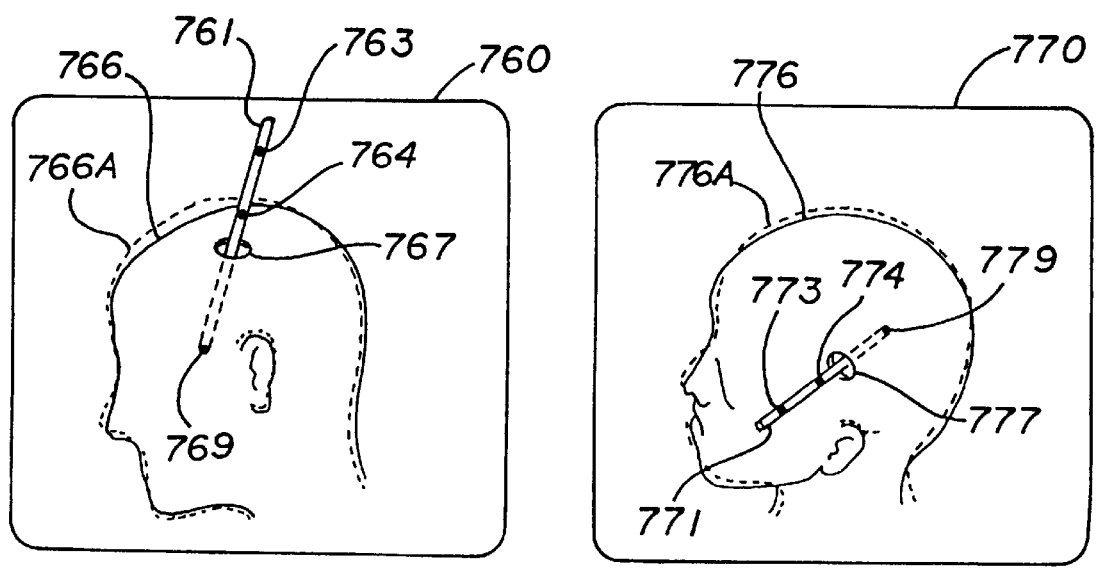
FIG. 7

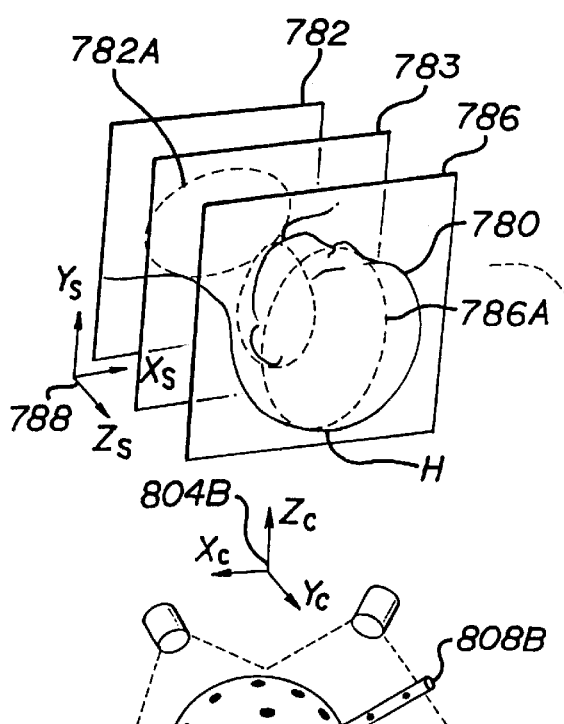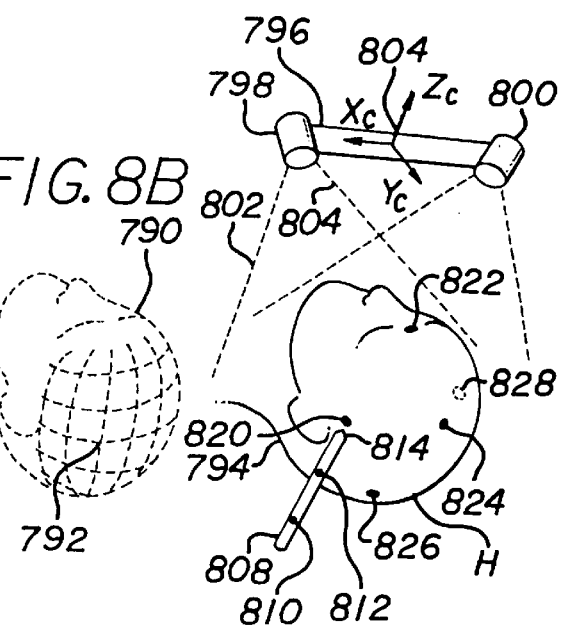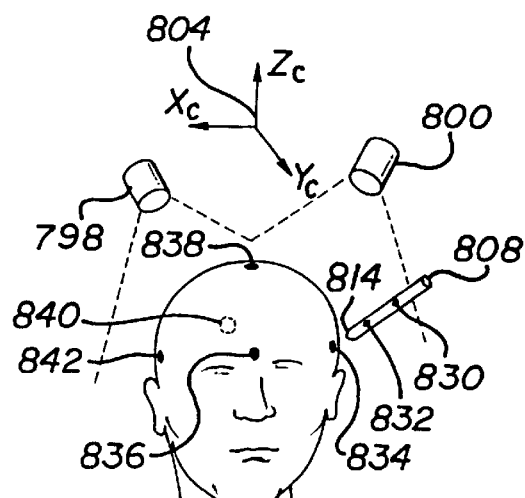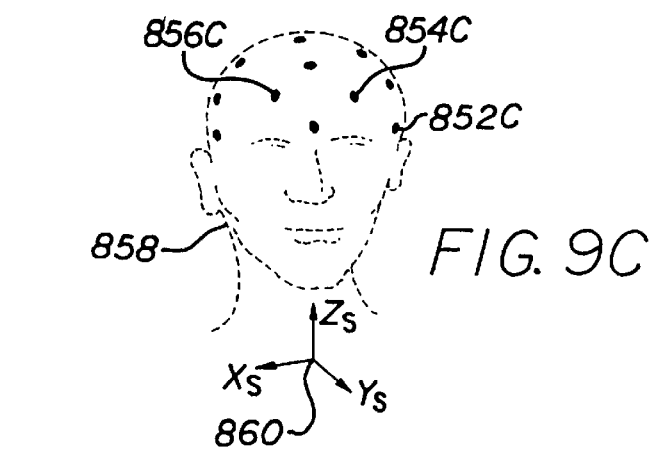

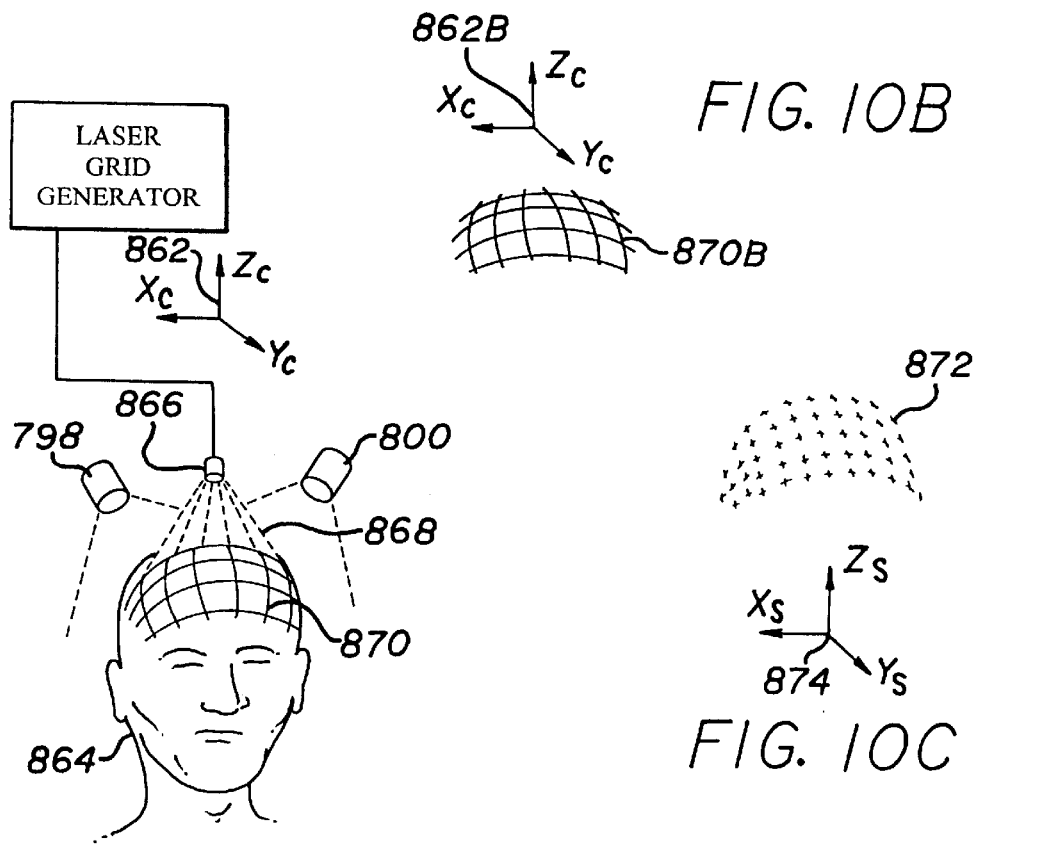
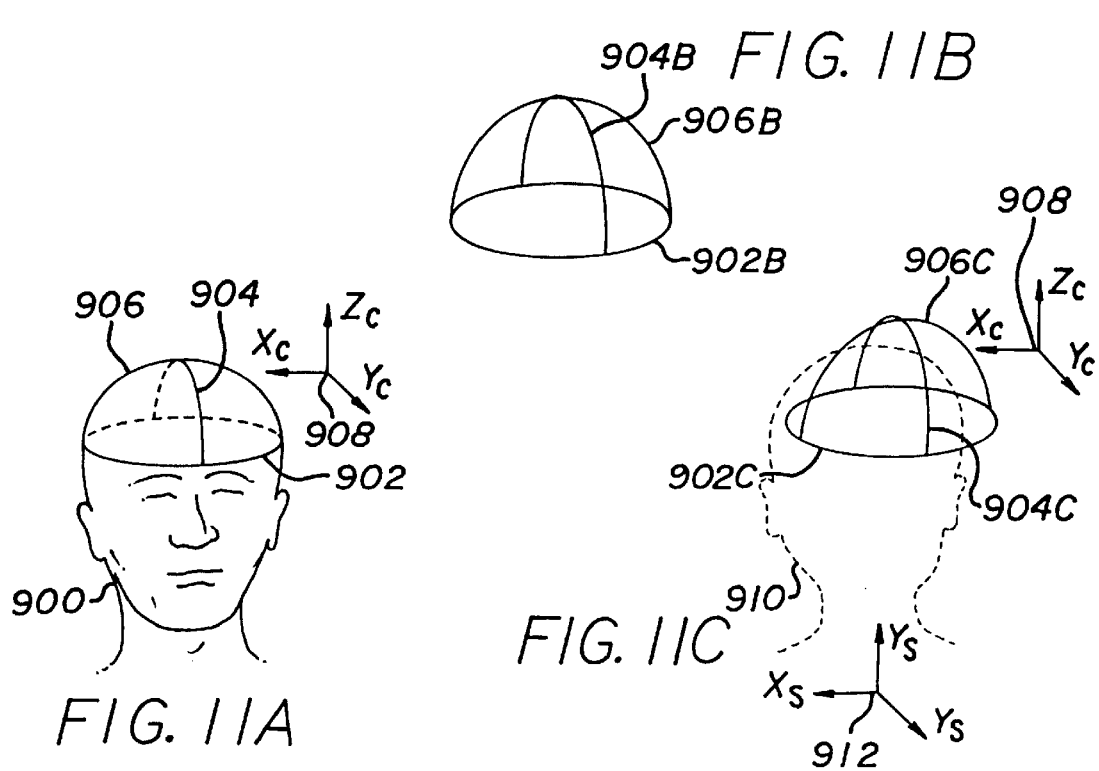

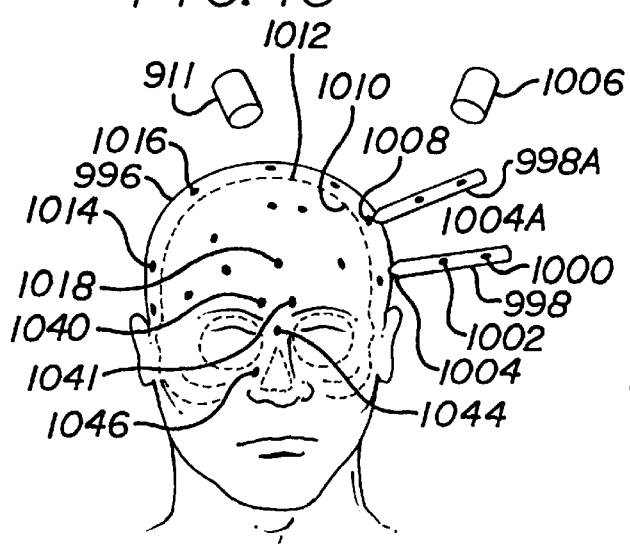
FIG. 16
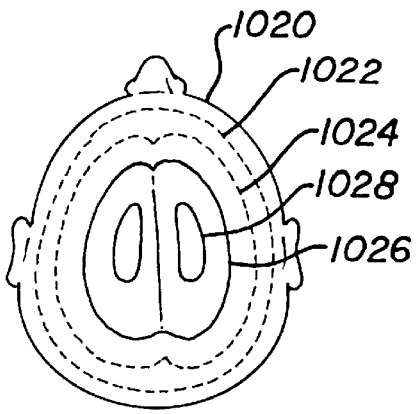
FIG. 17
FIG. 18
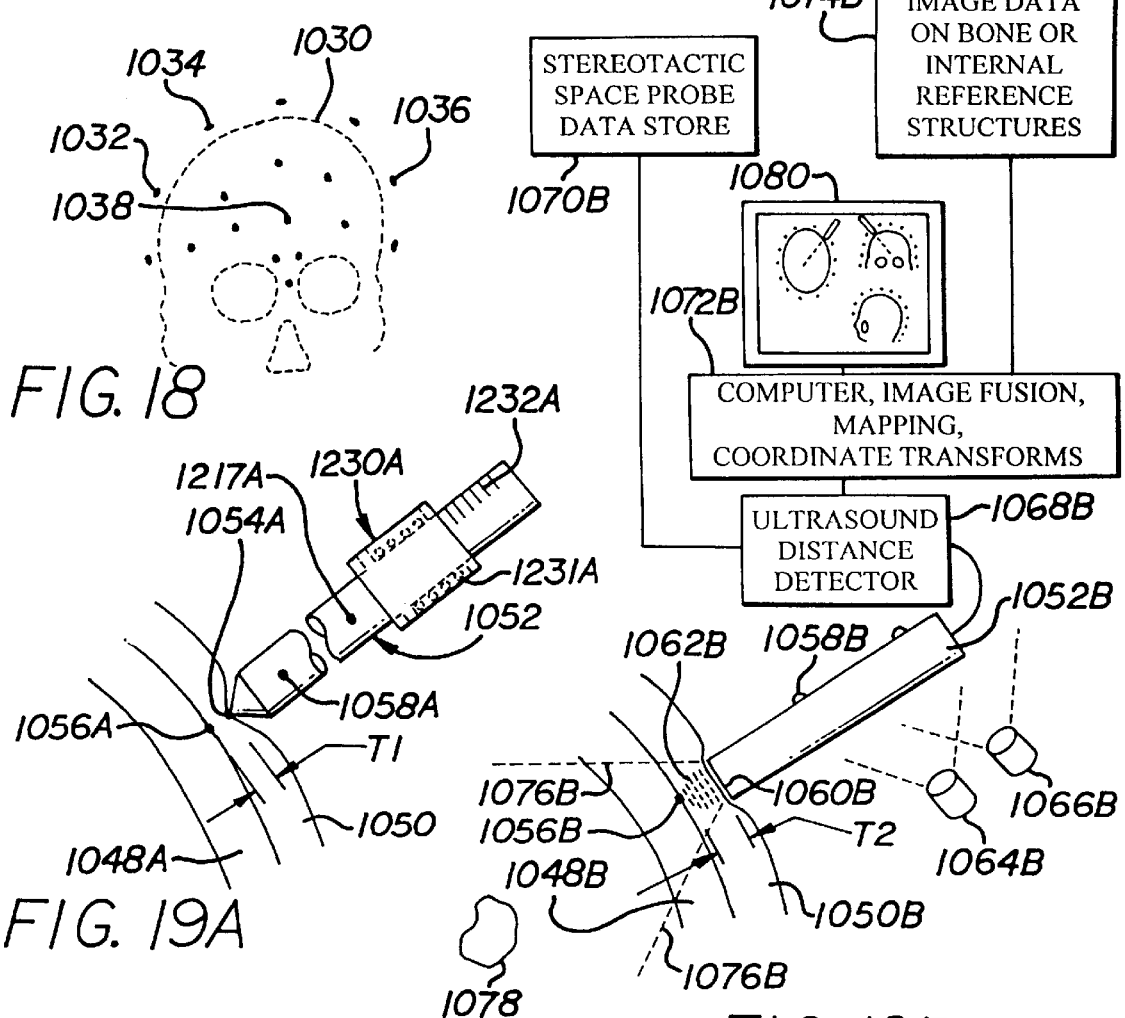
FIG. 19A
FIG. 19B

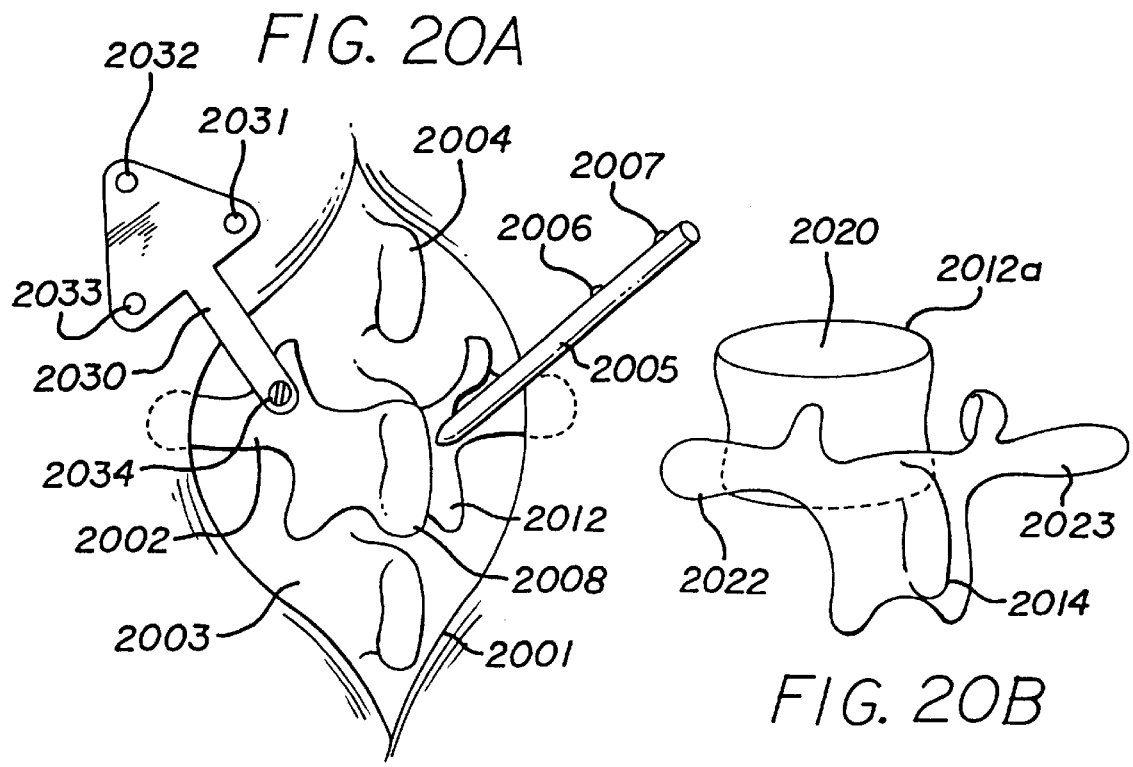
FIG. 20A
FIG. 20B
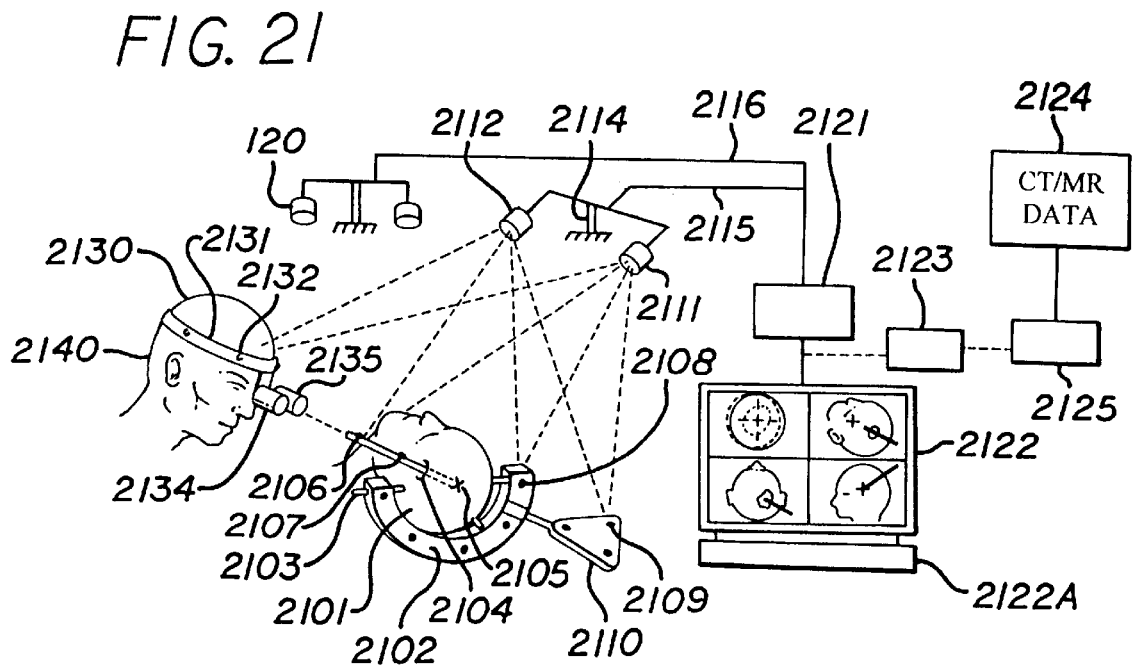
FIG. 21

SYSTEM AND METHOD FOR STEREOTACTIC REGISTRATION OF IMAGE SCAN DATA

REFERENCE TO CROSS RELATED APPLICATIONS

This is a continuation-in-part of application Ser. No. 08/441,788, filed May 16, 1995, which is a continuation of application Ser. No. 08/299,987, filed Sep. 1, 1994, which is a continuation of application Ser. No. 08/047,879, filed Apr. 15, 1993, now abandoned, which is a continuation of application Ser. No. 07/941,863 filed Sep. 8, 1992, now abandoned, which is a continuation of application Ser. No. 07/647,463 filed Jan. 28, 1991, now abandoned.

BACKGROUND AND SUMMARY OF THE INVENTION

The concept of frameless stereotaxy is now emerging in the field of neurosurgery. Frameless stereotaxy involves quantitative determination of anatomical positions on a human body, say for example a human head, based on image data taken from a CT (computed tomography), MRI (magnetic resonance imaging) or other well-known slice scanning techniques. The data from such image scans may be entered into a computer to generate a three dimensional graphic representation of the human head. This is of great value to surgeons, as they may visualize where they will be operating relative to this data field. Surgeons may thus, plan their operations quantitatively prior to actually performing them, based on an anatomy visualization represented by the image data.

To date, the use of stereotactic head frames for fixing and orienting a head is commonplace. For example, see U.S. Pat. No. 4,608,977 issued on Sep. 2, 1986, to Brown and entitled: System Using Computed Tomography As For Selective Body Treatment. Such stereotactic head frames utilize a head fixation device, typically with some form of an index means, that may be visualized in scan slices or image data. Thus, the anatomical image data can be defined relative to the head frame.

Arcuate mounts or probe carriers may be fixed to frames to hold and guide a probe based on the anatomical image data. If use of the head holder and carrier can be limited, patient discomfort can be greatly reduced.

The headholder and localizer still may be used for general neurosurgery where only approximate target positioning is needed. For example, a space pointer may be directed over the anatomy and its position may be quantified relative to the stereotactic image data. The space pointer, analogous to a pencil, might be pointed to a specific location on the anatomy such that the location and the direction of the pointer, subsequently appear, real time, on the computer graphics display of the anatomical data. Such an apparatus has been proposed, using an articulated space pointer with a mechanical linkage. In that regard, see an article entitled "An Articulated Neurosurgical Navigation System Using MRI and CT Images," IEEE Transactions on Biomedical Engineering, Volume 35, No. 2, February 1988 (Kosugi et al), incorporated by reference herein. It would be convenient and effective if the space pointer could be mechanically decoupled or minimally mechanically coupled.

One objective of the present system is to provide a camera apparatus (optical) to visualize a surgical field and relate it via a computer graphics system to stored image data of the patient's anatomy. The relationship between the camera data and the image data is processed to quantitatively represent and indicate surgical instruments such as probes, microscopes, or space pointers in relation to the anatomy image.

Another objective of the present invention is to optically couple a space pointer or other equipment item to accomplish the same objectives as the robotic arm mechanically coupled space pointer, e.g. give ongoing positional correspondence between a location in a patient's brain and the tomographic image. The optical coupling frees the surgeon from sterility questions, provides an obstruction-free device, and avoids the encumbrances of a bulky mechanical instrument.

According to a method of "frameless" stereotaxy as described above, a camera system or navigator consists of a set of cameras viewing a surgical field, in relation to a patient's anatomy. Equipment or anatomy, e.g. probes, a microscope, or other surgical devices may be viewed and tracked by the cameras within the surgical field, and the position of these devices may be quantitatively determined. Various registration, mapping, transformation, or merging schemes may combine the image scan data of the patient's anatomy with camera system data. Various examples are shown and described involving index reference points on anatomy or equipment that may be used to correlate to the image scan data. Natural landmarks, contours, surfaces, or other reference marks are disclosed for combining image scan data of the anatomy with real time physical anatomy or equipment position data.

Other illustrative examples are disclosed for registration between the image scan data (e.g. stored data) and anatomy and equipment data (e.g. real time). The examples given may apply to the field of "frameless" stereotaxy, wherein a head frame or head clamp is placed on the patient's head after the image scanning is done. It may also apply to frame-based stereotaxy, where a head clamp or head frame is placed on the patient's head prior to image scanning. The methods and apparatus and the examples given herein may be used in a variety of fields, including interventive stereotaxy, stereotactic radiosurgery and radiotherapy, or general image processing to relate image data to an apparatus means or surgical or diagnostic equipment environment.

BRIEF DESCRIPTION OF THE DRAWINGS

In the drawings, which constitute a part of the specification and where the reference numerals indicate like parts, exemplary embodiments of the present invention exhibiting various objectives and features thereof are set forth. Specifically:

FIG. 7 is a perspective view of two cameras looking at the anatomical subject with corresponding graphic views both of the camera, readout and field of view and of the computer graphic representation of the same view;

FIGS. 8A, 8B and 8C show schematic diagrams of the image scan coordinate system space and associated image scan slices, reconstructed views of the image scan space, and the physical space of the patient in relation to external reference or detection apparatus (optical cameras) respectively;

FIGS. 9A, 9B and 9C show an embodiment in which reference spots or locations are determined in physical space relative to the coordinate system of the detector system (optical cameras); and these in turn are related to the coordinate space of the image scanner via reconstructed image scanner data;

FIGS. 10A, 10B and 10C illustrate the manner of imposing a grid or series of discrete points on a natural surface anatomy of the patient using a scanning laser and making use of this topography or grid to perform a surface optimization fit or otherwise visual or intuitive fit to a reconstructed or reformatted configuration of the image scan data associated with the surface anatomy or patient topography;

FIGS. 11A, 11B and 11C show the use of simple linear tracks which may be impressed over the surface of the patient's anatomy in different directions, these tracks represent loci of physical points, which may be fused, optimized and fitted, or otherwise merged with the reconstructed shape, topography, or outline of the patient's image surface anatomy in the image scan space;

FIG. 16 shows another embodiment of the present invention in which the external surface contour of the body and/or the margin of the skull is determined in physical space as a reference means;

FIG. 17 shows the relationship of the external contour of the skull to the external contour of the skin, these landmarks being usable as registration means for the frameless stereotactic digitizer;

FIG. 18 shows the relationship of externally determined physical points to the internal surface of the patient's skull and a schematic diagram of fusing these two data sets in shape so as to co-register them; and FIGS. 19A and 19B illustrate registration of the physical coordinate data corresponding to the patient's skull to the corresponding image scan data of the skull as determined from a CT scanner, possibly together with computer graphic reconstruction of the skull image and possibly with the adjunct of special depth probes or ultrasonic sounding devices;

FIGS. 20A and 20B are perspective views to show the application of surface swabbing on the spinal bone with a stereotactic digitizer to register the directions and dynamic reference frame of a spinal structure relative to image scan data of that structure;

FIG. 21 is a perspective and diagramatic view of an alternative embodiment for tracking a surgeon's head and surgical viewing loops relative to a surgical field;

DESCRIPTION OF THE PREFERRED EMBODIMENT

Figure 1:
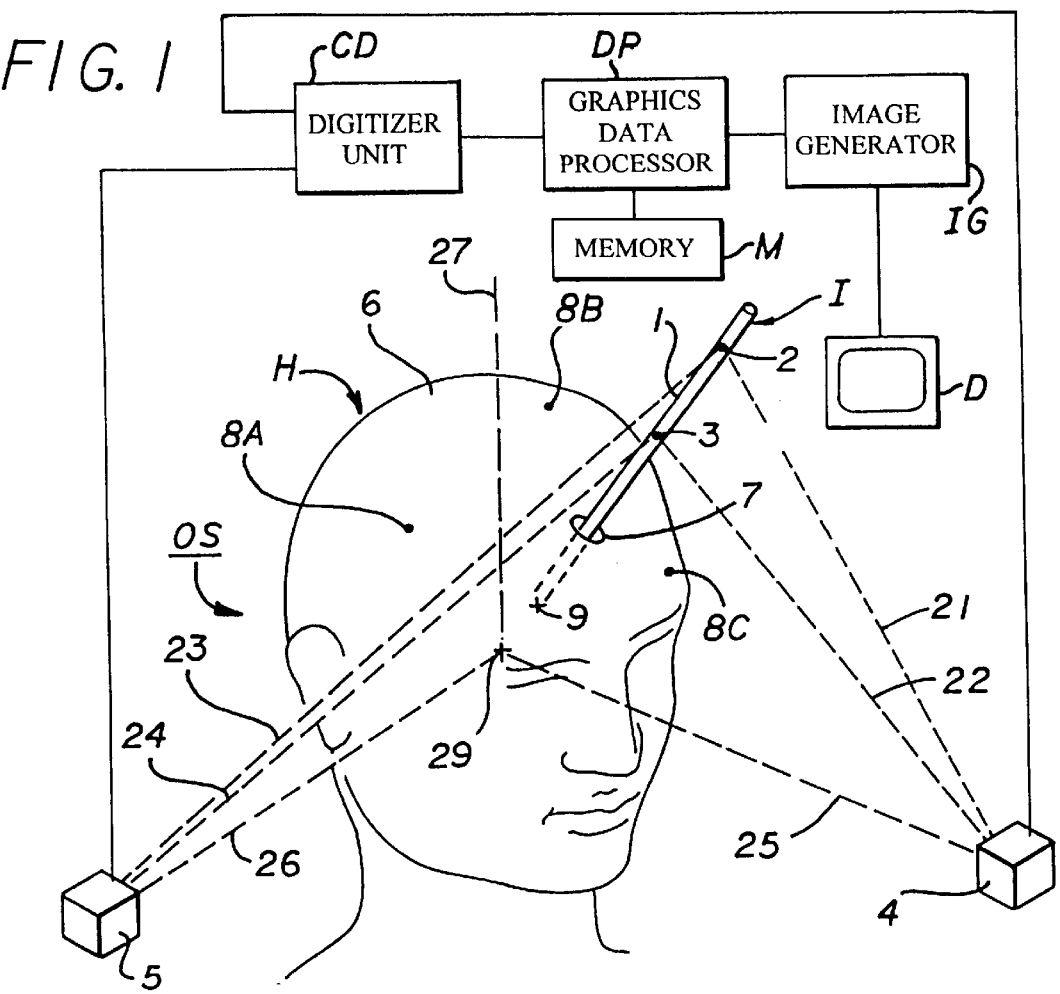
FIG. 1 is a perspective and block diagram of an embodiment of the present invention for providing a composite anatomy and instrument display.

FIG. 1 illustrates a neurosurgery setting, showing an object field that includes a patient's head H penetrated by an instrument I, that is, the patient is being operated on through a skull hole 7. As the instrument I, in the form of a probe 1, penetrates the head H, it is desired to know the depth, i.e. the positional relationship of that probe 1 to the head H. The relationship is visualized by combining position data on the probe 1 with data from some imaging means such as CT or MR scanners or angiographic X-rays showing internal views. The interior image data representative of the patient's head may have been previously accumulated and stored in a computer, as described in the referenced U.S. Pat. No. 4,608,977.

Referring to FIG. 1, the scanned three dimensional image data is stored in a memory M and supplied to a graphics data processor DP along with digitized view data (detector coordinates) from an optical system OS including a pair of cameras 4 (lower left) and 5 (lower right) and a digitizer unit CD. Various forms of index devices, as disclosed in detail below, identify specific objects and locations.

The composite data received by the processor DP is correlated as to compatible coordinates then processed for an image generator IG which drives a display unit D for depicting the probe 1 in relation to the patient's head H. The operations and techniques utilized in these components, as graphics data storage and organization, data processing, image generations, pixel processing, transformations, display techniques and related functions are disclosed in texts as "COMPUTER GRAPHICS: PRINCIPLES AND PRACTICE" by Foley, Van Dam et al, published by Addison-Wesley Publishing Company, published in 1982, Second Edition 1990. See also "PRINCIPLES OF INTERACTIVE COMPUTER GRAPHICS", Newman and Sproull, published in 1979 by McGraw-Hill Book Company.

The camera apparatus or system OS, includes the cameras 4 and 5, which may for example take the form of known devices, e.g. CCD Type compact TV Scanners with high resolution to provide data that may be easily digitized and displayed by the display unit D. Accordingly, position data is provided from the cameras 4 and 5 as disclosed in a book: Digital Image Processing, Second Edition, Addison-Wesley Publishing Company, Gonzalez and Wintz, 1987, incorporated by reference herein.

The use of stereoscopic imaging techniques, as by the processor DP, to map points sensed by the camera system OS in world coordinates is treated in a section 2.5.5 entitled "Stereo Imaging", beginning on page 52. As explained in the book, the camera system OS specifies the coordinates (X, Y and Z) of index light sources 2 and 3 on the instrument I. The subject also is treated in a book: Visualization of Natural Phenomena, by Robert S. Wolff and Larry Yaeger, First Edition, TELOS, The Electronic Library of Science, Santa Clara, Calif., 1993 (which is an imprint of Springer Verlag, New York), incorporated by reference herein. Specifically, see Chapter 3 entitled "Through Canyons and Planets," pages 66 and 67. Detailed treatment of cameras as imaging trackers appears in a book: The Infrared Handbook, incorporated by reference herein and prepared by the Environmental Research Institute of Michigan (1978) for the Office of Naval Research, see pages 22-63 through pages 22-77. See also, a book: Digital Image Processing, Prentice-Hall, Inc. by Kenneth R. Castleman, published in Englewood Cliffs, N.J. 1979, incorporated by reference herein and specifically a section entitled "Stereometric Ranging," beginning on page 364.

Essentially, the data specifying the location of the probe 1 is combined by the processor DP with the stored anatomy data from the memory M to drive the display unit D through the graphics image generator IG. Objects can be variously depicted, located and defined by index markers.

In FIG. 1, the cameras 4 and 5 are directed at a field including the patient's head H and the probe 1. The orientation and quantification of the camera coordinate data taken from the scan images in the video cameras is registered by index spots 8A, 8B and 8C placed on the patient's head. One alternative to these index spots might be a head ring (disclosed below) which is fixed firmly on to the patient's skull and has index markers on it which may be seen in the views from the cameras 4 and 5. When the index markers are in view of the cameras 4 and 5, the appropriate transformations are made by the processor DP based on the coordinates of the index markers 8A, 8B, and 8C which are known beforehand to the entire data set (CT or MR) of anatomy in the memory M. Thus, the reference points are used to relate objects in the camera fields of view to data for combination with the stored anatomical data.

In some applications, more than three point markers may be used for redundancy or better definition. As illustrated, the probe 1 in FIG. 1 carries two index markers in the form of light sources 2 and 3, which are visible within a certain range to the cameras 4 and 5. Thus, the orientation of the light sources 2 and 3 relative to the anatomy is sensed by the two cameras 4 and 5 and thus physical position of probe 1 relative to the stored CT or MR data on the head H also is known. Since light sources 2 and 3 are in a predetermined orientation relative to a tip 9 of the probe 1 (defined by object data), the actual physical location of the tip 9 relative to the anatomy may be computed in the processor DP.

With the locations of the index sources 2 and 3 specified, the orientation of the probe 1 may also be computed from the two camera views. Thus, the data accumulated by the cameras 4 and 5 provides data to display the orientation and the absolute position of the probe 1 relative to the scanned anatomy data. A slice of the anatomy can be displayed with the probe tip and accomplished by the image generator IG in real time as the probe 1 is moved. As the probe 1 position within the entry hole 7 is known, the tip 9 is graphically visualized on the screen of the display unit D along with stored anatomy inside the patient's head H. This is a most useful aid when exploring the interior of a surgical hole, as when the surgeon wishes to know the advancement of the probe or some other surgical instruments within that hole. The system may also be useful in planning the position of a surgical incision. By pointing the probe at the crown 6 of the patient's head H, the location is displayed relative to anatomy inside the head. Accordingly, the surgeon may make a judicious choice of an entry point.

The index light sources 2 and 3 may be LED light sources of very small dimension and may be powered by a battery located in the probe 1. Thus, the probe is not mechanically coupled to other apparatus and only optically coupled to the cameras 4 and 5. The optical coupling may be done in other ways. For example, there may be external light sources positioned nearby from which light is reflected by tiny index reflectors that function as the index light spots or sources 2 and 3 on the probe. The reflected light is detected by cameras 4 and 5 giving the same optical registration of the probe position as though the reflectors were sources of direct light from the probe itself.

Using known computer graphics techniques, recalibration of the entire optical system along with coordinate transforms and image manipulation is also possible. Cameras 4 and 5 may have principle optical axes, 25 and 26 respectively shown in FIG. 1. The cameras may be aligned to point in a plane and directed towards a common isocenter 29. Thus all rays in the field such as rays 21 and 22 as seen from camera 4 to the spots 2 and 3 or rays 23 and 24 which also connect the sources 2 and 3 on the probe to the camera 5 may be calibrated in the field of the cameras so that their exact angles relative to the principle rays indicated by 25 and 26 may be quantitatively determined and represented by signals defined in the digitizer unit CD. Once the quantitative orientation of these rays to the fiducial point sources 2 and 3 are digitized and determined numerically in the unit CD, then the position and orientation of the probe 1 may be calculated relative to the point 29 which has been recalibrated as explained below.

In the processor DP, the exact referencing of the coordinate system represented by axes 25 and 26 with their crossover point 29 and orthogonal axis 27 can be determined by further fiducial points on the anatomy itself, e.g. markers, spots or points 8A, 8B, and 8C. Natural anatomical fiducial points also may be used such as the tip of the nose, the ears or other bony landmarks. However, specific index points such as the points 8A, 8B, and 8C may be placed on the patient's scalp or crown 6, for example, and these may be used for reference transformation to relate the data sensed by the cameras to anatomical data. For example, the exact coordinates of the points 8A, 8B, and 8C may have been determined in space from the scan data previously and stored in the memory M. By knowing the exact coordinates of the points in the stored data space and knowing the position of other anatomy relative to them, and by determining the position as seen by the cameras 4 and 5 of these three fiducial points, the rest of the anatomy may also be registered in the camera's field by the processor DP. Thus the exact positioning of the fiducial points 8A, 8B and 8C correlates the graphic display of the anatomical data (display unit D) from the images. The points and resulting transformed data accommodate the registration with scanned data using techniques as well known in the art.

Also, the exact position of the probe 1 with its fiducial points or spots 2 and 3 may be set quantitatively into the field by the processor DP. This operation corresponds to a series of 3-dimensional coordinate transformations as explained in the referenced texts and is a straight-forward mathematical matter. Specifically, mathematical transformations are well known in the computer graphics prior art as treated in the textbook: Fundamentals of Interactive Computer Graphics, Addison-Wesley Publishing Company, 1982, Foley and Van Dam, incorporated by reference herein, see Chapter 7 entitled "Geometrical Transformations."

Figure 2:
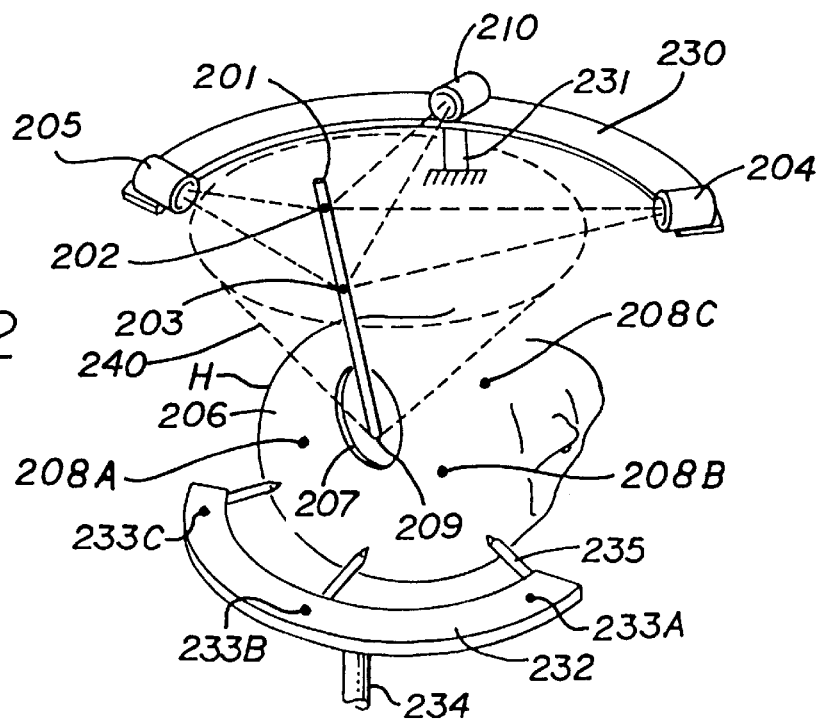
FIG. 2 shows an alternative component of the embodiment of FIG. 1.

FIG. 2 illustrates another embodiment of one position of the system as shown in FIG. 1. In this camera system, more than two cameras are involved. Cameras 204 and 205, as well as camera 210, are present and may be prealigned or not prealigned prior to surgery. They are anchored on a support structure 230 which holds them rigidly in place and that support 230, in turn, is clamped by a clamping means 231 to some stable object relative to the patient's head 206 such as the operating room table or the floor itself. Thus, the camera support structure 230, and the head holder 232, with the patient's head H are rigidly fixed together.

The headholder may be a standard headholder as conventionally used with pin fixation points 235 to the skull or head H as illustrated by the arcuate structure 233, which, as suggested is anchored to the operating table or to the floor by post 234 and, thus, the optical system above it and the head holder are stabilized relative to each other by means of their attachment to either themselves or to the operating table.

Again, the index points or spots 202 and 203 (light sources) represent the fiducial points for cameras, specifically the cameras 204, 205 and 210. By digitizing the field of these cameras, the position and orientation of the probe 201 is determined in space coordinates by the digitizer unit CD (FIG. 1). In addition, index reference points 208A, 208B, and 208C (FIG. 2) are provided which represent independent fiducial points on the patient's head H and which are observed by the cameras to check the stability as well as the coordinate reference frame continuously by monitoring the fiducial points on the anatomy itself. Note that somewhat similar index points 233A, 233B and 233C attached to mechanical structure (holder 232 affixed to the head H) can be observed for relating movement of the anatomy relative to the cameras (real time).

There is a typical range of motion of the probe 201 with respect to entry locations, which is practical in such operations illustrated for example by a dashed-line cone 240. The cameras 204, 205 and 210 may visualize the probe 201 and the fiducial points or spots 202 and 203 everywhere within the working cone 240. This is typically the range in which the surgeon will be introducing instruments into the cranial opening site 207.

It is clear that the positions of the cameras 204, 205 and 210 may be prearranged and precalibrated as fixed on the bar 230. This may be done and stored by the digitizing unit CD (FIG. 1) so that the cameras point isocentrically to the same location in that their visualization fields are precalibrated and preoriented so that everything within the field has a known calibration. This may also be easily checked by taking the platform 230 off at any given time and putting it on a phantom base or some other jig structure which enables instant calibration of the system. It is also true that the head holder 232 may carry fiducial light sources or fiducial marker points or spots 233A, 233B and 233C so that it may be referenced relative to the cameras and the entire system becomes an integral digitized calibrated system.

Figure 3:
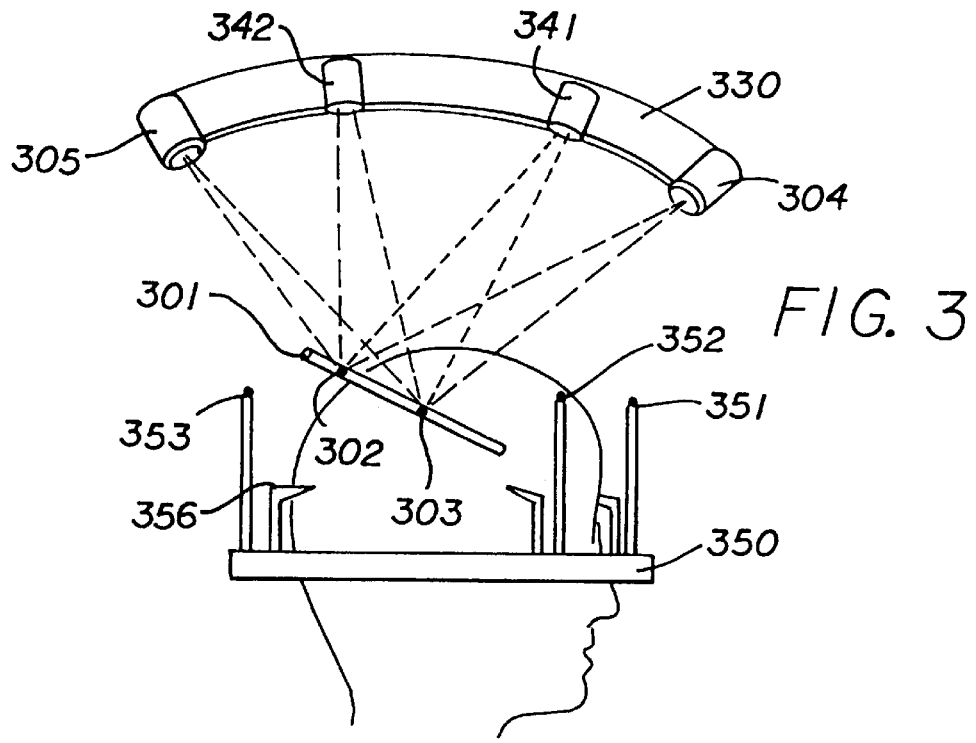
FIG. 3 shows another alternative component of the embodiment of FIG. 1.

FIG. 3 shows another alternative camera component or system element for use in a system as illustrated in FIG. 1, in which a pair of external light sources 341 and 342 are mounted on a bar 330 as well as cameras 304 and 305 for receiving optical signals. The cameras 304 and 305 are arranged and rigidly fixed to the bar 330 for positioning. The light sources 342 and 341 are also arranged and attached to the bar 330 so that they aim towards a probe 301 which carries reflectors or other index spots 302 and 303 which reflect the light from the light sources 341 and 342. The cameras 304 and 305 detect the reflected light which is illustrated by the dashed-line light beams as shown in FIG. 3. In this way the probe 301 does not require an energy source or active light sources, but may be merely a reflector of light. It is also noteworthy that the probe may take the form of a long reflective linear structure or may have other arrangements for the fiducial index points instead of the linear reflector 302, which is coaxial with the probe. Various pattern recognition structure of this type may be detected by the cameras 304 and 305 with the corresponding digitization of the probe position and orientation in a digitizer unit CD (FIG. 1).

In the example of FIG. 3 a headring 350 is affixed to the patient's head by a series of head posts 356 anchored securely to the skull. On the headring are fiducial elements 351, 352 and 353 which serve as index points and reference points that may also be detected optically by the cameras 304 and 305. In this way, the ring 350 represents a platform and corresponding coordinate system basis, the position of the coordinate system being referenced by the fiducial points 351, 352 and 353 and monitored in terms of its relative position to the bar 330 and its associated cameras. In this way the entire operative setting may be monitored for any differences in position and position differences may be corrected for if they are determined by the computer graphics associated with the cameras 304 and 305.

It is notable that the need for discrete index points such as 302 and 303 on the space pointer may not be absolutely necessary. Pattern recognition algorithms in a digitizer or computer would form data from cameras 304 and 305 to recognize the shape of the space pointer 301. Thus, the quantitation of its position in the field need not be done by discrete index points on the instrument.

The major advantage of the camera sensed probe structures illustrated in FIGS. 1, 2 and 3 is that they are mechanically decoupled from the observing cameras and thus there are no encumbrances of mechanical linkages such as a robotic arm as has been proposed in the past. It is also true that these probes may be made relatively simply and are made to be disposable so that the surgeon may throw the probe away after the procedure without incurring great expense.

Figure 4:
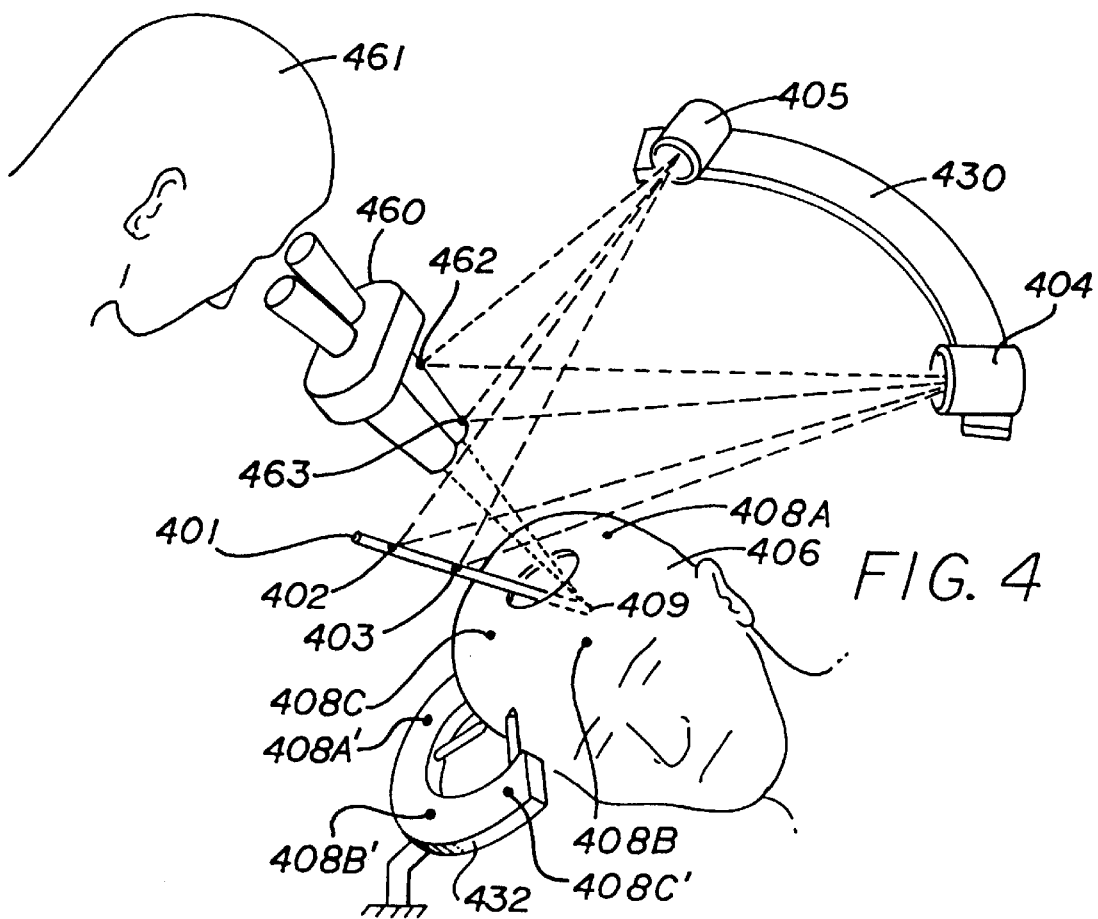
FIG. 4 shows still another alternative component of the embodiment of FIG. 1.

FIG. 4 shows another component embodiment for use in systems of the present invention with optical digitizing viewing means which involves not only a probe 401, but also an operating microscope 460. The objective here is to determine quantitatively the relationship between the current position of the patient's head 406, anatomy within the head, the space probe 401 and the operating microscope 460. The principles are somewhat similar to those described above with reference to the system of FIG. 1.

The patient's head 406 is stabilized by headholder 432. The microscope has index markers or spots 462 and 463 which may be LED point light sources or reflectors as explained above. Similarly, the probe 401 has its index points 402 and 403. Cameras 404 and 405 are affixed to base platform spots 430 and view a field embracing the microscope, probe, and patient's head.

Optical index points 408A, 408B, and 408C may be attached to the patient's scalp or to the headholder (points 408A', 408B' and 408C') to provide referencing to the stored data anatomy of both the probe and the microscope. By this sort of viewing, the relationship of the position of the microscope 460 and its orientation relative to the anatomy may be determined as explained above. Thus, the display unit D (FIG. 1) shows the field of view in which the microscope is viewing relative to the anatomy. In that regard, see the above referenced textbook, Computer Graphics: Principles and Practice.

When computer graphics representations of the anatomy have been made, then computer graphics of the field view with a microscope may also be represented on the graphics display means and, thus, the relationship between what the surgeon 461 is seeing and the computer constructed field may be made. This is very important in planning as well as performing interactive surgical resections. At the same time, the probe 401 may be inserted into the field and the position of its tip 409 may be represented within the actual microscopic viewing field of the microscope 460. The entire surgical array of instruments may be represented graphically so that interactive correction and management of the operation may be made by the computer systems. One may also put other instruments within the field such as scalpels, probes and other devices which the surgeon commonly uses, these being indexed by fiducial marks or simply visualized directly by the cameras and representations of them put onto the graphics display means. Thus, the entire field (instruments, microscope, anatomy) can be tracked in real time.

Thus by the index points, spots or sources that have been alluded to in FIGS. 1 through 4 and the associated embodiments, the various structures including anatomy, probes, microscopes and other instruments may be related in one graphics display along with stored scan data. It should also be noted that once this relationship has been established, the cameras which sense the actual objects themselves may make direct overlays of the objects as seen with the graphic representation of these objects as calculated from the imaging prior to surgery. Thus, direct correspondence of shapes and objects may be instantly ascertained by the operator by merely overlaying the graphics display and the actual display together on the same graphics screen.

There are other variations of the embodiments disclosed above involving the use of computer graphics techniques. One does not need to have, for example, two or more video cameras pointing in the same plane. They may be non-coplanar and there may be an array of them to encompass a much larger field of space. Such a multi-camera display may be precalibrated or not precalibrated. The cameras may be monitored and stabilized by fixed fiducial points somewhere in the field so that the entire registration and synchronization of all cameras would be possible.

The mounting on which the cameras are held may be movable and changed interoperatively to optimize the position of the cameras while maintaining registration with the subject field. The orientation of the cameras relative to anatomy, a microscope or a probe may also be done without the need for fiducial lights such as sources 2 and 3 in FIG. 1 or index fiducial points 8A, 8B, and 8C in FIG. 1. Overall correspondence of the shape of the subject as viewed by the camera may be overlaid and optimized in its matching to the graphics representation of the anatomy taken from the images.

Graphic rotation of the image data may be done so as to register the direction of view of the camera relative to the anatomy. This correspondence would then be done by shapes of subjects in the real field vs. shapes of subjects in the graphics field. Such optimization of the two shapes may be done and the direction of the camera thereby determined relative to the field of view. Once that is done, the orientation of the probe 1 or any other shaped object related to a probe may similarly be registered from the camera's point of view. Pattern recognition algorithms may be used to determine the orientation of the probe 1 relative to the orientation of the other subjects such as the head and its orientation relative to the cameras.

The present invention also recognizes the possible use of a single optical camera. Although the examples above illustrate the use of two or more cameras, there is utility in even using just one camera to view the surgical field. It provides a two-dimensional representation in a projected view of the field. One may use this representation and the graphic representation from the image data to register the two views and, thus, align the graphic display in a "camera view". Thus pointers in the field of the camera may be registered directly on to the graphic display view. For example, a pointer moving on the surface of the skin would be registered relative to the graphic view so that you would know where that point is moving relative to this quantitative data that represents the skin and other anatomical structures below the skin. This would have more limited usefulness, but it may also be important. Thus, the application of mounting a single video camera to view a surgical field and representing that visual field on a graphic field so as to bring the two fields into alignment by manipulation of the graphic field in the computer has utility in the surgical setting.

Figure 5:
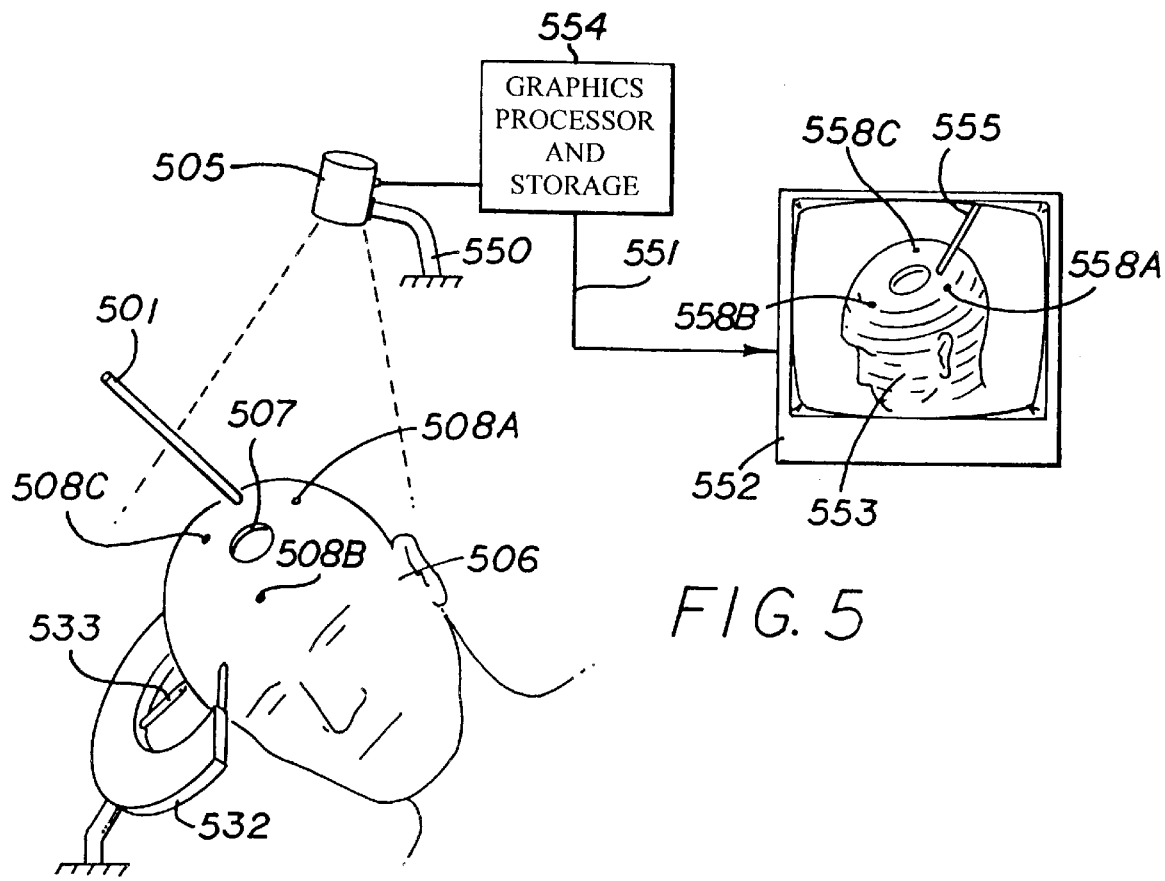
FIG. 5 is a perspective and diagrammatic view showing a generalized, single camera embodiment of the invention where the camera is coupled to a computer graphic means and the view of the camera looking at the patient anatomy is related to image data from image scan means so as to register the camera view and the image data to quantify the camera view field.

In the context of the disclosure relating to FIG. 1, FIG. 5 illustrates more specifically the use of a single optical viewing camera and registration of its field by computer graphics to image data. In FIG. 5, a camera 505 which has been anchored via arm 550 near the surgical field, views the patient's head 506 and other objects nearby. The camera 505 is connected through a processor box 554, via cable 551, to a computer graphics display unit incorporating a screen 552. The computer graphics box 554 incorporates computer calculation means and storage means to produce an image as represented on the screen 552. The data in the storage means (in box 554) may be provided from a scanning source, e.g. a CT or MRI scanner or it may be a magnetic tape with corresponding data on it. The camera 505 is viewing the head and a representation of the head shows on the screen 552 together with image data indicated by the contours 553. To illustrate some exemplary structure in the field, a probe 501 is shown which is seen as representation 555 on the screen 552. Also, there is a surgical opening 507 and for completeness, the index marks 508A, 508B, and 508C which aid in orienting what is seen by camera 505 to the graphics image data seen on screen 552.

The headholder 532 and associated pins 533 hold the head 506 firmly relative to the camera 505. As shown on the screen 552, the corresponding index points 558A, 558B, and 558C are shown on the screen as well as the actual image of the anatomy and the space probe represented by image 553. Thus, if computer graphics representations of the same anatomy are simultaneously put on the screen, for example, in a different color, then those image data may be scaled, translated, and rotated such that they register with what is seen by the field of view of camera 505. By so doing, one has in perspective view a registration of the camera data with the image data. Thus when one looks at the probe representation 555, on the computer graphic screen 552 of the actual probe 501, one may see immediately the correspondence of that probe relative to the quantitative stereotactic image data anatomy. Thus in perspective view, one is relating the position of the probe to that stereotactic image data anatomy, and this may be a very useful adjunct to surgery. For example, if one wished to know where to make the surgical opening 507, one may move the probe 501 in actual space relative to the anatomy until one sees the probe in perspective view with its tip over the desired point relative to the image data anatomy seen on screen 552. That would instantly tell you that this is the place to make the surgical bone opening, for example. There are many other illustrations of the use and power of this one-camera approach.

Figure 6:
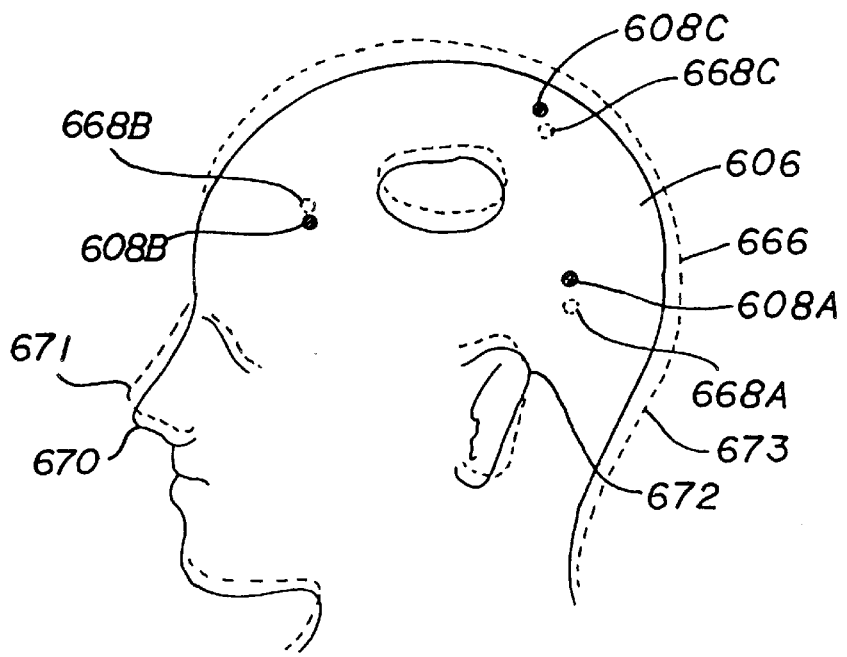
FIG. 6 is a diagrammatic view illustrating how camera field data would be registered in position and orientation to analogous image scan data on the same computer graphic display.

FIG. 6 shows how one might register camera anatomical data to image machine-acquired anatomical data as described in the paragraph related to FIG. 5. For example, in FIG. 6 the outline 606 represents the actual contour of the patient's head as sensed by the camera 505 in FIG. 5. Also, the points 608A and 608B and 608C are shown as dots and these too are sensed by the camera. Furthermore, anatomical landmarks such as 672, the tip of the ear, and 670, the tip of the nose, may be seen by the camera 505 in FIG. 5.

The dashed-line contour in FIG. 6 shows a similar contour reconstructed in a perspective view from, for example, CT slice image data. Such image data may be stacked, may be surface rendered, and may be viewed and oriented from any different direction by computer graphics manipulation. Thus, it is possible to take such "dashed" image data representations, scale them proportionately, rotate them in space, and translate them, such that when you view the dashed and undashed contours on the computer graphics console, the operator may easily trim in the image data or the dashed line 666 such that it matches exactly the solid line 606 on the computer graphics screen. Such treatments of computer graphics data are disclosed in a textbook: Principles of Interactive Computer Graphics, McGraw-Hill Book Company, Newman and Sproull, 1979, incorporated by reference herein. For example, moving parts of an image is specifically treated in a section 17.3 at page 254. Also, in a similar way, one may make computer graphic manipulations to register the correspondence of the image points from the camera 608A, 608B, and 608C with the corresponding index points 668A, 668B, and 668C, which are illustrated by dashed points in FIG. 6. Registering these two sets of the same physical points in the computer graphics would be an tractable way of registering the entire two perspective views. Similarly, anatomical landmarks which are identifiable such as the computer graphic representation of the tip of the ear 673 and the tip of the nose 671 may be represented and corresponded to the analogous points 672 and 670 from the camera data. The use of different colors, color washes, color transparencies, and other powerful graphic standards as well as mathematical algorithms to optimize the correspondence of these two perspective views are easily put into play at this point to do the job.

FIG. 7 illustrates another embodiment of how more than one camera may be used for computer graphic registration and corresponding quantification of an optical view. In the upper portion, one sees two cameras 704 and 705, pointing at arbitrary non-identical directions towards the subject 706. The fields of view are shown with the dashed lines. There is a cranial hole 707 with a probe 701 in it to the depth of the brain with the tip 709 inside the head. Index points 702 and 703 on the probe may or may not be present and are analogous to those discussed in FIG. 1.

Each of the cameras will have views as illustrated in the lower portion of FIG. 7 and are displayed on the computer graphic display means 760 and 770. The display means 760 represents, for example, the view of camera 704 and one sees the solid line 766 which is the optical outline as seen by camera 704 of the patient's head. Similarly, the probe 761 is seen through the burr hole 767. By computer graphic translation, rotation and scaling, one may adjust the computer graphic view so that it matches the anatomical view, i.e. the computer graphic perimeter 766A indicated as dash line exactly matches 766. In this way, one knows that one has reproduced graphically with the dashed curve the projected view as seen by 704.

Analogously, camera 705 will have its view as seen in graphic display 770 of the outline of the head 776 being matched to the graphic outline of the head 776A. Obviously, index marks, grids or lines on the patient's scalp might help in this registration of the two camera views. Once these views, however, have been registered, uniquely identifiable points in both views may give information on the exact 3-dimensional coordinates of those identifiable points relative to the anatomy as seen from the image data. For example, the points 763 and 773 are identical and correspond to the physical point 702 on the probe. On each of the views 760 and 770 this point represents a projected line as seen from the respective camera. The two lines from the two cameras intersect at a unique point and this may easily be determined as a unique 3-dimensional point referenced to the data from the image scanner as stored in the computer. Thus, the two points 702 and 703 may be determined quantitatively in space relative to the anatomical data, and thus, the quantitative position of the probe and any point on the probe may be determined relative to the image data. In particular, the end of the probe represented by point 709 which is in the depth of the brain and indicated on the graphics display as 769 and 779 respectively may be determined, i.e. the 3-dimensional coordinates of that point relative to the 3-dimensional image anatomy may be determined. Thus, there is no particular need for special index marks as shown in FIG. 1. Mere registration of existing anatomical structures relative to camera view and the image data would be sufficient for a full 3-dimensional representation of any instrument such as the probe in FIG. 7 relative to the anatomy. Using special angles such as 90° or stereoscopic views of the cameras may be convenient for such 3-dimensional registration without prior calibration.

It also should be said that for fixed camera positions, the subject itself might be moved so that the optical representation matches the graphic representation. In most cases, it would seem simpler to do the movement of the subject's image data via software, than moving the anatomical subject relative to the cameras, however, both methods may be used for registration of the respective images.

The use of such camera registration with image data eliminates any need of camera field calibration or the need to know relative camera angles.

Recapitulating, the disclosed system relates to the use of optical and image data correspondences to register and quantify the position of surgical tools such as the space probe or the microscope illustrated in the above examples. It is related to making the associated mathematical transformation from a coordinate system or perspective view seen by one or more cameras to a stereotactic coordinate system related to image data or a corresponding reconstructive perspective view of image data and associated coordinate information from such image data. It relates to the correspondence between objects both anatomical or surgical in a camera view to objects either anatomical or of an index or marker nature as represented from scanner data or extrapolated from scanner data in a computer or computer graphic system. This was given as a specific example from FIG. 1 in the relationship of a mechanical space pointer to index marks and these, in turn, to corresponding quantitative positions in space where index marks are known from image data. Registration of the camera viewing data to the image data may or may not involve index marks, index lines or index localizer devices. It may be done as illustrated in FIGS. 6 and 7 by visual or computer theoretic optimization of registration of camera and image data or camera and reconstructed image data or enhanced camera or manipulated image data. The invention further generalizes the concept of "a camera" to other camera-like devices. These might include an x-ray camera or an x-ray source which is point-like and projects through the anatomy to give the image on a detection plane at the opposite side of the anatomy. This data may be projectively reconstructed as though it were reflected light from a single camera as illustrated in the examples above. Thus, the invention subsumes the field of generalized camera viewing or projected image acquisition relative to CT, MRI or angiography acquisition from other imaging means and the registration thereafter to make correspondence between these two image acquisition modalities.

Using more than one camera enables the determination of three-dimensional coordinates and depth of perception. The examples on FIGS. 1 through 4 illustrate this by use of a probe with two fiducial points on it that may be seen and digitized by the two camera views. This invention relates to the use of a video camera to quantitatively relate to graphic display data taken from other imaging means. The correspondence of the data are illustrated by the embodiments above and the discussion above, but those skilled in the art may think of other implementations of the same invention concept. For example, the use of two fiducial points on the probe may be extended to other types of optical fiducial means such as lines, other arrays of points, other geometric patterns and figures that may be recognized easily by computer graphics, artificial intelligence, etc. The two points illustrated in the figures may be replaced by a line of light and one or more discrete points to encode the direction of the object. The object itself may be recognized by the computer graphics as a line merely by having it of a reflective material or a particular color. The space pointer, for instance, may be white or green and thus show up differently on the video display so as to recognize it as the pointer. The FIGS. 8–19 and descriptions of those figures further provide other illustrative aspects, structures and features.

FIG. 8A graphically illustrates a setting in a CT scanner, such as an X-ray tomographic scanner, MRI scanner, PET scanner, or other scanning means. The patient's head H represented by anatomy 780 is being scanned by an image scanner as well known in the art to produce three dimensional data that may be stored and viewed as slices or planes. Some scan planes are illustrated by planes 782, 783, and 786 passing through the patient's anatomy. External contours of the head H are illustrated by the dashed lines 782A, 783A, and 786A, respectively.

Anatomical features of the body within the slices may be displayed in great detail and are very beneficial for clinical, therapeutic, and diagnostic purposes. Typically, the slices are parallel or nearly parallel, and have a coordinate frame within the plane, usually referred to as the X and Y axes, defined by the scanning system, and typically dimensioned in millimeters, although they may be in pixels or other dimensions.

The spacing between the slices and the position of the slices may also be typically calibrated by the scanning system or the associated couch. Thus, there is a reference system or coordinate system typically associated with the scan slice system which may be referred to as $X_s$, $Y_s$, $Z_s$, somewhat as depicted by the coordinate system 788 in FIG. 8A. Thus, there is a frame of reference or coordinate system associated with the scanner. Its origin is arbitrary.

FIG. 8B indicates a reconstruction of data representing the patient's anatomy 780 in quasi-three dimensions or in graphical form, illustrated by the dashed line 790, which represents the outer contour, and the grid or pin cushion spots 792 aligned over the image of the patient's surface anatomy. The surface of the anatomy 780 may be rendered as a tiled surface or a grid or mesh of lines, or a cloud of points, or merely an image-scan data set represented by coordinate points or mathematical points associated with the reconstructed surfaces based on the image slice surfaces or external contour surfaces as illustratively represented by contours 782A, 783A, and 786A in FIG. 8A.

Thus, the raw image scan data or slice data as stored may be processed and automatically segmented in terms of its external contour or the surface of the skin, as illustrated by contours 782A, 783A, and 786A, and may be reconstructed, merged, averaged, interpolated, or otherwise re-rendered in graphics or by a computer to represent and display a surface or slice of the patient's head in any number of ways, including splined views, pyramidal, or pin-cushion views, etc. As explained above, the display may also depict instruments or other devices in real time locations.

The mathematically reworked or reconstructed surface may comprise the actual contours defined by the external contours 782A, 783A, 786A, rendered as a series of lines in the coordinate space 788 of the scanner. Alternatively the surface may be an interpolated surface which does not have the actual mathematical coordinates of the original slice perimeters defined by the contours 782A, 783A, and 786A, but rather is a mathematically interpolated or otherwise rendered surface that is continuous in its surface nature, or step-wise or piece-wise continuous over its surface, or merely a cloud of mathematical points representing a surface anatomy, surface features, surface landmarks, etc.

FIG. 8C shows a representative portion of the system of FIG. 1 with the patient's head H represented physically in real space. Specifically, fragmentarily shown is a detector system 796, which, in this specific embodiment comprises two cameras 798 and 800, illustrated as viewing the scene that includes the patient's anatomy 794. The viewing angles are represented by the dashed lines, for example, 802 and 804, which subtend some field of view for each of the cameras 798 and 800. The detector system 796 is merely one component of the total system as illustrated in FIG. 1.

A coordinate system (see FIG. 1, unit CD) associated with the detector system 796 which is represented by the coordinate axes $X_c$, $Y_c$, and $Z_c$. This may be referred to as the camera coordinate system, the stereotactic system, or the physical coordinate system. The detector system, which may comprise optical cameras, and in alternate forms, sonic digitizers, radio signal devices, or other devices, may detect or track positions or points within the physical space and assign physical points and coordinate values associated with the coordinate system represented by the coordinates $X_c$, $Y_c$, $Z_c$ illustrated and referred to as the coordinate system 804.

In the case of systems using optical cameras, as illustrated in FIGS. 1–7, the cameras may actually view the relevant scene to its full extent if they are two-dimensional cameras, and thus the actual object may be seen in stereoscopic stereotactic visualization and identifiable points within that field, seen by both cameras, may then be assigned a coordinate value in physical space, which may be associated with the stereotactic coordinate system 804.

Also shown in FIG. 8C is the space probe 808, which carries optically-visible points or index spots 810 and 812. Other patterns of such points may be used. Its tip resides at a location 814, which may or may not be in a known position relative to the points 810 or 812. This example shows that if the points or index spots 810 and 812 are visible and trackable to the camera, for example if they are LED light-emitting diodes or reflectors of light which may be detected by the cameras, then the position, orientation, angulation, and time rate of change of the position of the probe 810 may be tracked in the coordinate system 804 by the cameras, and indeed the tip 814 of the probe may be tracked in physical space.

Thus, if the probe touches a point, such as point 820 on the patient's physical surface (anatomy), the coordinates of that point 820 may be registered relative to the coordinate system 804. Similarly, other points such as points 822, 824, 826, and 828 may also be present on the surface of the patient's anatomy, for example the patient's head 794. These points may then be specific points in physical space residing on the surface anatomy of the patient. They may or may not bear any specific relationship to points which are visualized in the image space of the patient's anatomy, as illustrated by the slices 780, 782, and 784. However, the position of these physical points may be correlated, merged, optimized or fitted to the image surface rendering of the image space, as illustrated by the object in FIG. 8B. Thus, the relationship between the stored image surface 790 and the actual surface 794 may be correlated and thus the transformation mapping, registration, or coordination of the coordinate system 788 of the image scanner may be related to the coordinate system 804 of the detector system, i.e. the coordinate system of the stereotactic or physical space.

Alternatively, the index spots 820, 822, 824, 826, and 828 may be actual physical index markers which are, for example, radiopaque, and thus discernable in the physical space and also in the image scan space, or they may not be discernable in the image scan space. For example, if they are natural landmarks or simply arbitrary points which have no one-to-one or obvious relationship to the data taken from the image scanner or the reconstructed data of the image scan, then the merging, fusing, mapping, or optimizing of the physical points such as 820 to the image reconstructed surface has to be done in a mathematical, visual or heuristic way.

FIG. 9 further illustrates this concept. For example, in FIG. 9 a space probe 808 is shown with index markers 830 and 832 wherein the probe has a tip or position or virtual tip 814 which may touch off a point of an arbitrary nature 834. The surgeons or operators may select this point arbitrarily. The detector system (illustratively represented by the cameras 798 and 800) is shown viewing the scene as in FIG. 8, and associated with their stereotactic coordinate system 804. The coordinates of each of the exemplary points 834, 836, 838, 840, and 804 may be determined since the detector or camera system may track the position of the probe and the probe tip and has a basis of data, e.g. "knows," when the probe touches these points as well as what the coordinates of the probe tip are. Therefore the detector or camera system "knows" what the coordinates of these points are.

As mentioned, these points may be arbitrary and not predetermined. The operator may randomly select or establish these points over the surface anatomy or the patient. Alternatively the points may be natural surface points with some degree of uniqueness, such as the tip of the nose or the tip of the ears, which would also qualify as index surface features or surface landmarks which do not require placement of a specific radiopaque or man-made object on the surface.

FIG. 9B illustrates how a cloud of points may be established over the surface of the patient's head. For example, the probe 808B is shown pointing at a point 852. A multiplicity of these points are illustrated, (for example, by the points 854 and 856), all over or encompassing a larger surface of the patient's head. This "cloud" of physical points thus constitutes a set of data relative to the stereotactic coordinate system 804B, which provide digital or coordinate representation of the physical features, surface contour, or landmarks associated with the physical patient's anatomy.

In FIG. 9C, a cloud of physical points is again illustrated by the points 852C, 854C, and 856C, being the analogs of points 852, 854, and 856 from FIG. 9B. Each point has a coordinate position relative to the defined coordinate system 804B (FIG. 9B) associated with the cameras. Shown in FIG. 9C is a dashed head outline 858, which is reconstructed or derived from the image scan data, as illustrated in FIG. 8A. The dashed outline may consist of a tiled mathematical surface based on the external, segmented contours of each of the scan slice images such as illustrated of 782, 783 and 786 in FIG. 8, or it may be a cloud of points associated with the scan image data. None of this image scan cloud of points corresponds in a one-to-one or direct or pre-determined way to the cloud of points illustrated by point 852C of the physical space. The dashed structure or data 858 has, on the other hand, a coordinate representation or a coordinate mapping into the coordinate frame 860, represented by the axes $X_s$, $Y_s$, and $Z_s$ associated with the image scanner itself, as described in connection with FIG. 8A as the frame 788.

As may be seen from FIG. 9C, by representing and merging the cloud of points (represented by point 852C and the dashed surface 858 together), a mapping can be achieved of the same or common object in physical space with the same or a representation of the same object in image space and thereby correlate the coordinate system 860 of the image scanner to the coordinate system 804B of the stereotactic detector system or the physical coordinate system.

One may see, for example, that the cloud of points, as represented by point 852C, is slightly misregistered (in this case, shown as being shifted to the right on FIG. 9C from the dashed outline 858). For example, by showing each of these representations of points via a computer graphic workstation on a visualization screen (see FIG. 1), such as a cathode ray tube and visualizing the clouds of physical points and the mathematical image surface in three dimensions on such a visualization screen, or by projecting that data onto various two-dimensional views or planes, and then scaling, translating and rotating the cloud of physical points relative to the image surface 858, one may achieve a merging of these two representations of the patient's anatomy, one in physical space, one in image space, to determine a mapping or correspondence or transformation between the image scan coordinate system 860 and the physical coordinate system 804B.

FIG. 10 shows another component variation embodiment, method, and apparatus of achieving a transformation between two coordinate systems or reference systems of the scanner and sensed patient's anatomy.

FIG. 10A generally indicates a stereotactic coordinate system 862 with the detectors, such as cameras 798 and 800, for viewing the space which includes the physical anatomy 864, for example the patient's head. The cameras 798 and 800 are representative of the detection system (FIG. 1).

A laser scanner 866 also is shown in FIG. 10, casting rays of laser light, illustrated by dashed lines 868, onto the surface of the patient's head 864. The result is a pattern, array, grid, series of light spots, or other optically detectable array of light points illustrated by the lines 870 over the external contour of the patient's head 864. The cameras 798 and 800 may detect such a pattern from light 866 and determine the spatial position in the coordinate system 862. The array of light from 868 is, therefore, a casting of light which then reflects back into the cameras 798 and 800 to give a quantitative or reconstructed or representative view of the external surface or features of the patient's anatomy.

In FIG. 10B the grid 870B is associated to grid 870 in FIG. 10A. They are represented in a coordinate position or reference to the stereotactic or camera coordinate system 862B. Thus, this data, which is referred to as physical surface data or natural surface feature data is stored (see FIG. 1, memory M) and rendered graphically and may be rotated in three dimensions on a graphics display means so that one may visualize its orientation position and scale and stretch it appropriately as one wishes using computer graphics techniques (see FIG. 1, image generator IG).

The grid 870 may be stored as a set of data points, may be interpolated as a surface, may be approximated by mathematical functions or parametric curves or surfaces to suit the situation of mapping to the image data, or for appropriate ease or manipulation or efficiency. Thus, one may achieve a set of stereotactic computer data which is representative of the patient's anatomy and which is referenced to or in the coordinate space of the coordinate system 862B of the stereotactic apparatus or detection system or other apparatus which is located near to the patient's anatomy. In FIG. 10C a cloud of points such as the point 872 is shown that may be a rendering of, reconstruction of, mathematical surface tiling of, or reformatted, three-dimensional representation of the image scan data from the tomographic scanner, as would be analogous to the dashed lines 790 and 792 in FIG. 8B. This surface rendering 872 would have a coordinate representation or mathematical position within the coordinate or reference frame of the image scanner, which is represented by the coordinate frame 874 in FIG. 10C. If both the structures 872 and 870B are rendered in a computer graphic computer and on a computer graphic screen, they may be translated, rotated, scaled, perspective viewed, or otherwise manipulated mathematically or physically or visually with a "mouse", joystick, rotation ball, or other means so that they may be overlapped, merged, and optimized in their position, one relative to the other.

Mathematical algorithms such as least square fitting or chamfer algorithms or other minimization algorithms of surfaces, volumes, clouds of points, etc. may be invoked to make this merging between the image or structure 870B and the image or structures 872. When this merging has been appropriately done, then there is a merging or referencing or transformation or mapping between the coordinate system 862 of the physical space or detector system and the coordinate system 374 of the image scan coordinate system. Thereafter, a mapping of every point within the coordinate system 374 may be made to the coordinate system 862B and vise versa. That is to say, a point in the physical space of the patient's anatomy 864, which may or may not be on the surface of the patient's anatomy but may for example be in the depths of the physical anatomy, may then be mapped over to a coordinate point in the image space of coordinate space 874, and thus be correlated to the image scan slices, as for example the slice data represented by scan slices 782, 784, and 786 in FIG. 8A, and thus to the representative tomographic slices with the varying density data or image data as characteristic of X-ray, tomography, or MRI slices.

Thus, a point in the tomographic slice space may be mapped into the position in the physical space, or a position as determined in the physical space may be correlated to a position in the image scan space. This may be very useful in the case of planning an operation or an intervention stereotactically or determining during the course of the operation if a probe such as the probe 808 in FIG. 9A is put onto the surface or into the depths of a patient's anatomy, the position of the tip 814 in physical space may be determined and visualized in the image space of the image scanner, i.e. in the coordinate system such as 788 in FIG. 8A or represented on each of the slice renderings or three-dimensional volumetric renderings of the image scan data such as the slices 782A, 783A, and 786A, as illustrated schematically in FIG. 8A.

FIG. 11 shows yet another illustrative process and embodiment in which the patient's anatomy 900 is represented and a series of lines such as the line 902 in a quasi-axial plane, 904 in a quasi-sagittal plane, and 906 in a quasi-coronal plane may be described over the surface of the patient's head. This may be done by tracking the tip of a probe such as the probe 808 in FIG. 9A over the surface while tracking the position of the tip by the cameras 798 and 800 so as to determine and store the mathematical position of each of these lines 902, 904, and 906 in the coordinate space 908 representative of the physical space of the detector cameras (not shown in this FIG. 11A).

The lines 904B, 906B, and 902B as shown separated (FIG. 11B) may be segmented and isolated and representative of the topology of the surface of the patient's anatomy 900 and rendered or parameterized in the space of the stereotactic coordinate system 908 of the detectors.

FIG. 11C illustrates again the dotted line 910 which is a rendering in the image space of reconstructed or actual image slice data representative of the patient's anatomy or the external surface of the patient's anatomy, and also illustrates the superposed lines such as 906C, 904C, and 902C representative of the physical contours of the patient's head in the physical coordinate system represented by 908. The lines such as 902C, 904C, and 906C may be more complex in nature, may be more numerous in nature, do not have to be in the quasi-axial, quasi-sagittal, and quasi-coronal planes, but may be described or swabbed over the entire surface of the head in any number, density, complexity, or configuration as one wishes. These may be done in a non-predetermined way or in a predetermined way, and they may be done in a way that is referenced to natural landmarks such as the midline, sagittal midline, or coronal midline of the patient's anatomy or not referenced to such natural geodesic lines or landmark lines. In any case, once they are mathematically represented or graphically represented relative to the stereotactic coordinate system, they may be rendered, and merged, oriented, overlapped, or mapped to the representation or graphics rendering of the image scan data as represented by the dashed line 910 in FIG. 4C. The dashed line is, of course, rendered relative to the image scanner coordinate system represented by the coordinate frame 912 in FIG. 11C.

FIG. 12 shows yet another exemplary process in accordance with the present disclosure with the merging of the image scan data to the physical detection coordinate system via merging of physical points, anatomical points, reference points, surface features, lines or contours on the patient's anatomy to a representation or rendering or reconstruction of the images of the patient's anatomy from an image scanner. As indicated above, the points 920, 922, 924, 926, and 928 may be non-predetermined or predetermined points, spots, index marks, or merely arbitrarily selected surface contact points on the patient's physical anatomy. This is analogous to the points in FIG. 8C, and again, their positions may be determined by a probe means, or they may be determined by simply touching the anatomy on the surface of the patient's head and observing where that touch point is with respect to the cameras 798 and 800 in FIG. 8C, and since unique physical points as seen in the two camera views of cameras 798 and 12 may be determined physically in space relative to the coordinate space of the cameras as illustrated by 804 in FIG. 8C, then the coordinates of the set points may be determined in that coordinate space. These points need not correspond directly or in any theoretical way to points that are visible in the image scan data, as shown in FIG. 8A. Indeed, there may be no correspondence whatsoever between these points, since these points may fall between the gaps between slices, or they may be beforehand indeterminate with respect to the slice coordinate space. On the other hand, this is not a requirement, since these points may be points that are identifiable both in physical space and in the coordinate images, and thus in the coordinate space, but this and the parent application are not restricted or limited by that condition.

Figure 12B:
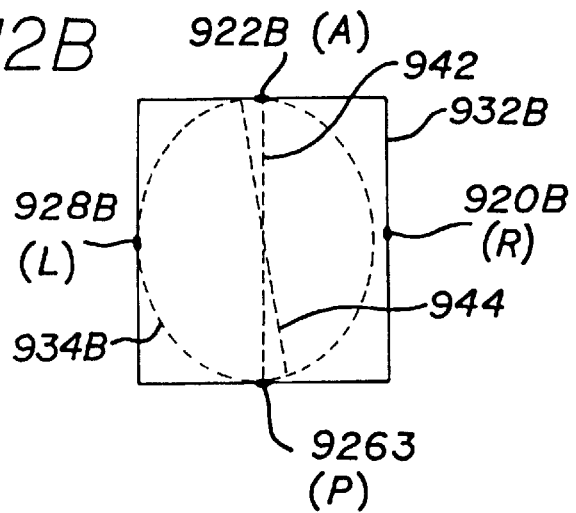
FIGS. 12A and 12B show the use of discrete points that may be detected, determined, or coordinated within the sphere of detection, which form a perimeter, outline, or fencing around the patient's head, which may be used to translate and rotate into a position so as to best fit or approximate the contour or external extremities of the patient's anatomy as visualized by the image scan data.

The point 922 at the anterior (A) medial portion of the head may be selected as being approximately on the midline of the patient's head; that is to say, on the brow or between the eyes and thus centered on the head. The point 920 on the right side of the patient's head may be located approximately centered above the ear or at the level of the auditory miatus or opening of the ear or some other anatomical point or approximately some anatomical landmark. Similarly, the point 924 at the superior (S) portion of the head may be approximated at the very top or of maximum point of the patient's head, and this may be only approximate. The point 926 at the posterior (P) portion of the head may be estimated or be the extremum of the crown or occiput on the back of the patient's head. Point 928 on the left (L) portion of the patient's head may be symmetrically or reflection symmetric to the point 920 on the right side of the patient's head. The points 920, 922, 926, and 928 may be approximated on a plane by a fixture, jig, or head band which may be put around the patient's head so as to place them on a plane for some convenience reason, but this is not a requirement at all, and they may be relatively arbitrarily placed. Once these points in the physical space are arbitrarily placed and the coordinates are registered or known relative to the coordinate system such as 804 in FIG. 8C of the detectors, then the process of merging these points to the coordinate space of the image scan data as the coordinate system 788 in FIG. 8A may be carried out. More points or fewer points, as illustrated in these examples, may be used. FIG. 12B shows a quasi-axial view or a projective view looking down or approximately down from the top of the patient's head, and the projections or projected views of these points may be seen and represented by the points, dots or spots 920B, 922B, 926B, and 928B. All of these points may not actually lie in a plane in the three-dimensional situation, as in FIG. 12A, but in projection they may all be seen from a given projected view, for example, along a line approximately perpendicular to the axial planes of the head. The perimeter in FIG. 12A, illustrated by 932, might have a left, right, front, back, and top representative of a cube or a parallelepiped which passes through or intersects the above-mentioned points, and thus frames the head or bounds the head for some convenient graphical or mathematical transformation condition.

The frame or boxing perimeter may be inputted as graphics reference data into a computer graphic workstation or system (see FIG. 1) along with the coordinates of the individual points. Thus, in the view in FIG. 12B, the perimeter line 932B illustrates the projection of this perimeter or the approximate projection of the perimeter.

Figure 12A:
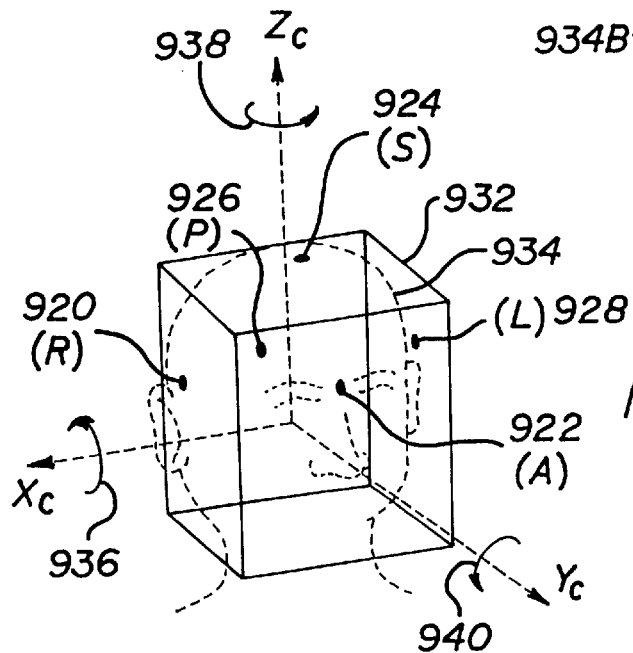

In FIG. 12A, a rendering of the patient's anatomy is again illustrated by the dashed line 934; and in FIG. 12B, the projection of that image-rendered contour or external anatomy is indicated by the projection line 934B. Actually, the projection line 934B may be an average, or an accumulation, or a cluster of lines as in topographical lines viewed from a given direction. Now a translation of the dashed FIG. 934 may be made so as to confine it within the box 932, and rotations around the $X_c$, $Y_c$, and $Z_c$ axes, as indicated by the arrows 936, 938, and 940, may be made of either the box 932 or the computer-rendered image representation 932 so as to best bound the head within the box or match the dashed contour or perimeter to the points, for example 922.

In FIG. 12B, for the particular projection, the dashed line 942 may connect the points 922B and 926B. The dashed outline or perimeter projection 934B of the image of the patient's head may have a midline line represented by the dashed line 944. Thus, a rotation of the line 944 into the line 942 would approximate a better angular registration around an axis such as the axis $Z_c$ in FIG. 12A so as to register the dashed curve 934B properly within the frame 932B. Translation of the dashed perimeter 934B along the axes which are in the plane of the figure or plane of the paper will optimally bound or improve the bounding of the box 932B with respect to the line 934B. By such an iterative procedure, one may fit the image rendering of the patient's head to the bounds or physical boundaries of the patient's head imposed by the points such as the point 922 in FIG. 12A. This is yet another means of shifting, translating, rotating, and scaling the patient's head so that the coordinate reference frames of the scanner and the physical reference frame may be matched, and thus transformed or mapped one onto the other.

Figure 13A:
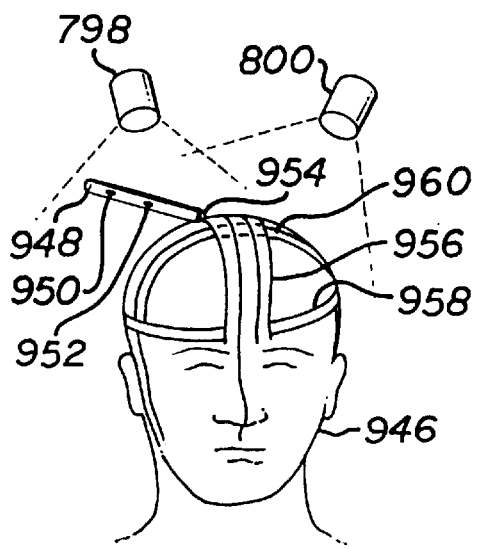
FIGS. 13A and 13B show another method of surface swabbing using a space probe which is digitized, detected, or tracked by the external detection system (for example, optical cameras) the swabbing lines then forming physical external contours in the coordinate space of the detecting system, which may be in turn merged, compared, fused qualitatively, quantitatively, or mathematically with the outline of the patient's anatomy as visualized on the image scan data.
Figure 13B:
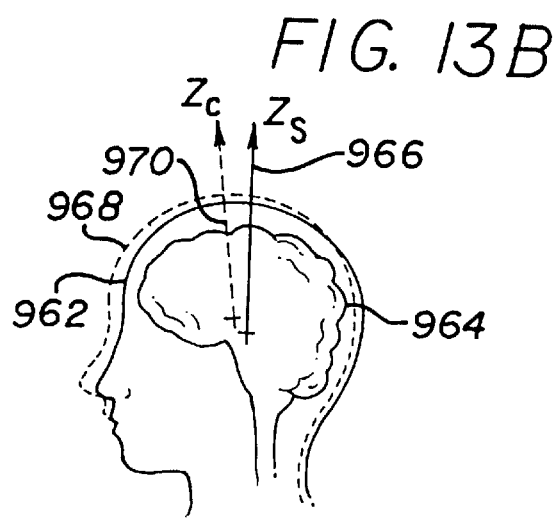

FIG. 13 again shows a patient's anatomy 946 and a probe 948 with visible reference points 950 and 952, tracked by a detection system (see FIG. 1) fragmentarily represented by cameras 798 and 800 such that the tip of the probe 954 may be observed in the coordinate space viewed by the cameras. The probe is shown to be swabbing the external surface of the patient's anatomy 946 and, as a consequence, the lines such as 956, 958, and 960 are being traced out over the surface of the patient's external anatomy. They are parameterized and known in mathematical space relative to the physical coordinate system, for instance as referenced to the cameras 798 or 800. FIG. 13B shows a quasi-sagittal view of the patient's anatomy represented by the solid line 962. This may be the external contour as seen on a reconstructed CT sagittal slice, or it may be a sagittal slice from an MRI scan. With such a slice, one may observe not only the external anatomy, but also, the brain and internal anatomy represented by the solid line 964. Thus, the internal parts of the patient's head may be rendered. A vertical axis $Z_s$, illustrated by the line 966, is shown, which may be the axis associated with the image scanner along the couch direction or the slice direction. The dashed line 968 may represent one of the quasi-sagittal lines 956 of FIG. 13A, or may represent a cluster or average of all of these quasi-sagittal lines. The physical line of FIG. 13A represented by the dashed contour 968 is slightly misregistered in this projection from the external contour 962 of the image scan. As seen there may be a vertical axis $Z_c$, labeled 970, associated with the coordinate frame of the cameras and associated with that contour 968, which is approximately in the axial direction relative to that contour. A rotation and/or translation of the dashed curve 968 may make it fit best or nearly fit to the line 692 associated with the external contour or in the image scan. By this way, and by a manipulation of these two sets of data, the physical data or the swabbed line data and image scan data, a manual or computer theoretical mathematical best-fit may be made between these shapes, and thus a registration of the coordinate systems represented by the axes 966 for the scanner and the axis 970 for the cameras.

Figures 14A, 14B, 14C:
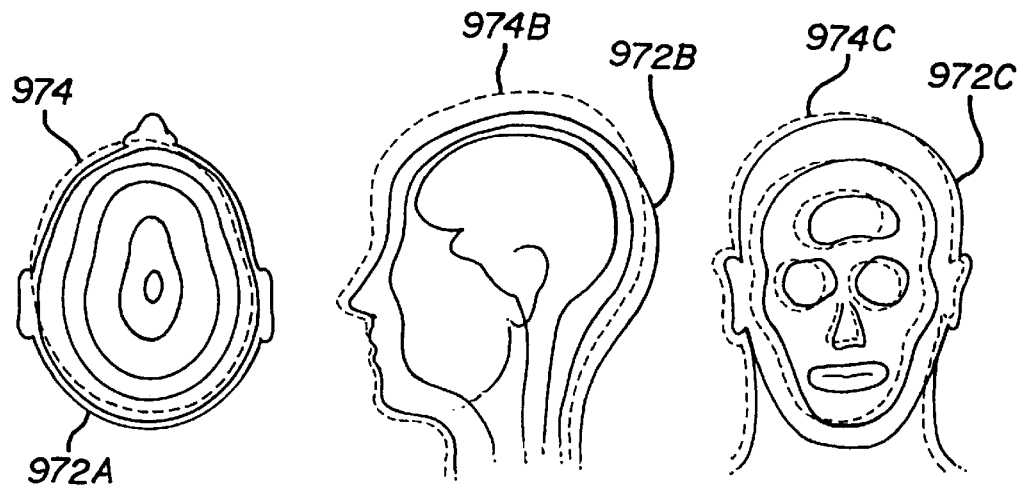
FIGS. 14A, 14B and 14C show the fusion, optimization, or merging of outlines derived from the image scan data of the patient's anatomy with contour plots or reconstructed plots from the physical data as detected by the detection system in three different views, axially, sagittal, and coronal, so as to heuristically or mathematically best optimize these two coordinate spaces.

FIG. 14 further illustrates how this type of matching may be taking place in three or more views. In FIG. 14A, for example, the contours in the axial planes, or quasi-axial planes, or reconstructed planes approximately axial from the image scan data are represented by the solid topographical contours illustrated by 972A. These are aggregated or accumulated in the downward view from the top of the head, and thus are shown as topographical contours in FIG. 14A. The dashed contour 974A might represent a contour from a swabbing line or collection of swabbing lines, as illustrated by the contour 958 in FIG. 13A. By moving the dashed contour 974A so that it best fits the outer perimeter 972A, graphically or manually a reasonable registration of the patient's anatomy may be achieved in the physical and image space, and thus registration of the coordinate systems for the cameras or detectors and the image scanner. FIG. 14B shows an analogous situation, as described essentially in FIG. 13B, of the solid contour lines 972B representing the image scan data in a sagittal view being registered or coordinate with the dashed perimeter 974B, which would represent the swabbed lines over the top of the head, such as the lines 956 in FIG. 13A. Again, translation and rotation, as described with respect to FIG. 13B, may bring these contours into overlap, registration, matching, or optimized positioning, one with respect to the other. FIG. 14C illustrates further, in a coronal or quasi-coronal view, where the solid contour lines 972C represent the reconstructions or projections in the para-coronal views from the image scan data. The dashed line 974C is a para-coronal contour which is representative of, derived from, or reconstructed from the swabbed lines such as 960 in FIG. 13A. By appropriate registration in these three views, a coordination of the physical object and the image-reconstructed object is made.

Such a coordination of image representations is done mathematically on a computer, by track ball or light pen manipulation, visually, or any other means which are known to those skilled in the computer graphics art.

Figure 15:
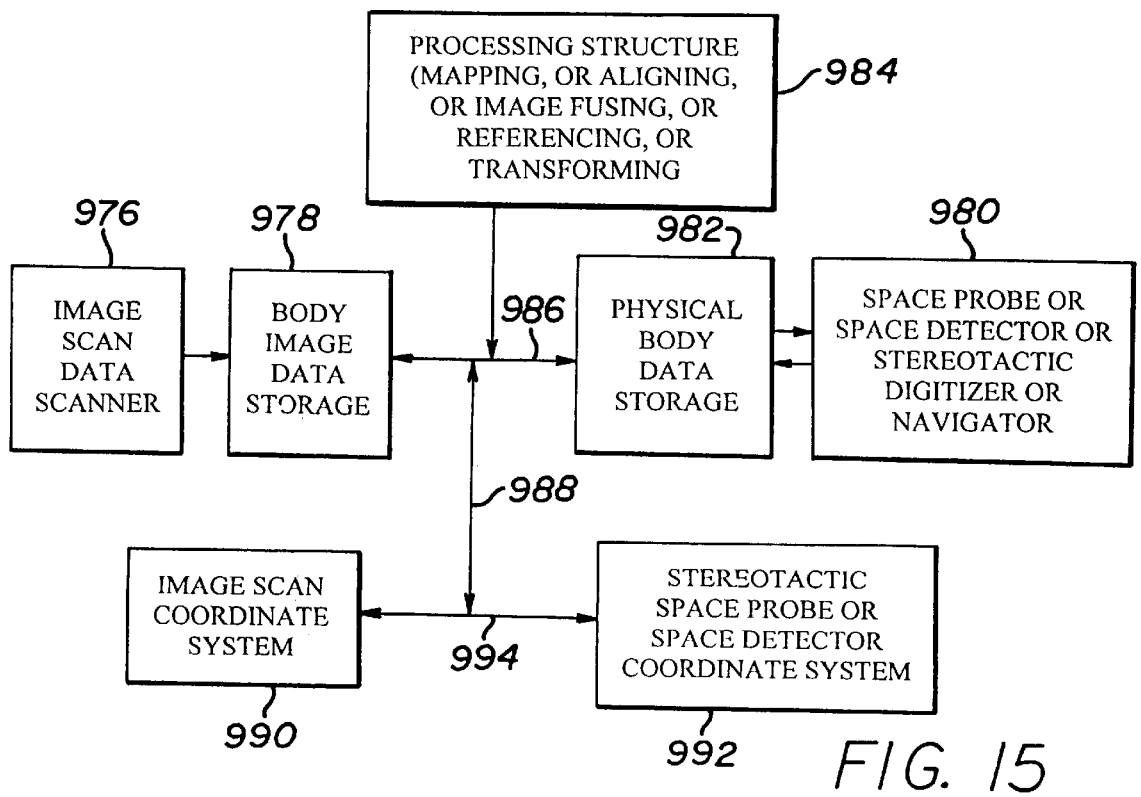
FIG. 15 shows a flow diagram which illustrates the coordination of image scan data to physical body data so as to provide a mapping or transformation between the coordinate space of the image scan data and the coordinate space of the detector or space probe device.

FIG. 15 shows a block diagram to merge the image scanner and the stereotactic space probe data. The image scan data is acquired by a scanner 976, which renders data on the physical anatomy related to that scanning, illustrated by the block 978. The space probe, space detector, or stereotactic digitizer or navigator, illustrated by block 980, provides some referencing of the physical anatomy, which provides physical body data 982 that may correspond to the body image data 978. This correspondence may be achieved by a mapping, aligning, image fusion, referencing, or some other transformation means illustrated by the block 984 so that the mapping, illustrated by the processing structure 984, takes place between the body image data and the physical body data. That mapping makes a correspondence, with data carried by the line 988, between a coordinate system associated with an image scan data 990 and the coordinate system associated with either the navigator or a detector system for the navigator or the coordinate system associated with an external apparatus which may be registered to the navigator, illustrated by 992. That mapping, therefore, providing data carried by the line 994, can then produce a transformation between image scan coordinate space from the image scan data and the stereotactic space of an external apparatus such as the digitizer.

FIG. 16 shows another example of the invention use, which relates to contour matching, but for contours or physical points which are not directly related in a one-to-one fashion or in an anatomically identical fashion to image structures seen in the image data. In FIG. 16, the patient's anatomy 996 is illustrated in this case by a head, or the skin of the head, although it may apply to any other structure in the body, as with all the examples in this patent. The probe 998 again has LED lights 1000 and 1002 as examples which are being tracked by an optical system (see FIG. 1) indicated by cameras 911 and 1006. The probe is shown with its tip 1004 at the surface of the skin, and this may set down or determine a physical point in stereotactic coordinate space of the cameras. The probe 998A is shown in another position, and its tip 1004A is indented to point 1008 on the skin so as to press it closer to a point on the underlying skull, which is represented by the point 1010 or the dashed contour 1012. The probe tip 1004A may never actually achieve the position of the skull 1010 below it; however, by pressing on the skin, it may approximate the position of the skull. The thickness of the compressed skin between the tip 1004A and the underlying skull position 1010 may be a relatively constant amount, or a tractable amount, or a predictable amount. Similar indented points may be set down or determined over the contour of the patient's anatomy such as points 1014, 1016, 1018, etc., represented by the black dots in FIG. 16.

FIG. 17 shows what might be a tomographic image through the patient's anatomy 1020. The skin is shown as the external solid line 1020. Inside, the dashed lines 1022 and 1024 represents the outer margin and the inner margin of the patient's bony skull. These are distinctly visible lines in both X-ray, CT, and MRI tomographic scanning and in other imaging means. The bone surface 1022, for example, is easily segmented and automatically determined by computer programs which do this, and such programs of segmentation or automatic margin determination are now practiced in the art of computer graphics. Furthermore in the body, one sees the contour line 1026, which is that of the external portion of the brain, for example, and the line 1028, which might be a contour of the ventricle in the brain. Each of these various structures may have varying density or varying image signal character and thus may be so-called segmented or defined in isolation, either manually or with computer graphic algorithms. The outer portion of the skull 1022, therefore, is identified by a multiplicity of tomographic slices, and this multiplicity of external contours of the skull is then rendered in a three-dimensional surface by spline or tile matching to the individual contours so as to produce a mathematical contour which is not identical to the individual slice contours but may represent the position of the skull in three-dimensional space of the image scan device or the coordinate system of the image scanner as discussed above.

FIG. 18 shows how a merging of dissimilar structures is achieved so as to register the coordinate system of the image scanner space with respect to the coordinate system of the camera detectors or other digitizing detectors, as the case may be. The dashed contour 1030 represents the reconstructed or image contour of the skull as identified in the image scan space. This may be a three-dimensional surface or it may be a profile contour or a set of discrete points as determined from the image scanning. Also shown in FIG. 18 within the coordinate system space of the cameras, referred to herein as the so-called stereotactic coordinate system space, are the positions of the coordinates as determined by the procedure referred to in FIG. 16. These points such as 1032, 1034, 1036, and 1038 are a cloud of coordinate points, which do not represent the same physical structure as the surface 1030. However, there is a topological correspondence that may be made between these structures once the data has been defined both in the physical or stereotactic space and, on the other hand, in the image space. Thus, a computer program may be used to do a least square fitting, or an image fusion, or an optimized fitting of the internal structure 1030 represented by the dashed surface to the cloud or collection of discrete points represented by the physical points 1036 so as to "best fit," or optimally place, or best position the dashed surface 1030 into the physical space of the physical points such as 1036.

By this procedure, the general shape of the skull, which follows roughly, and in some cases quite accurately, the general contour and shape of the scalp, allows the two shapes to be topologically set one inside the other. In this example, therefore, the physical index points on the patient's anatomy do not correspond to the same part of the anatomy as the points used from the image scanner. Thus, an embodiment is shown where dissimilar anatomical structures, one deeper in the body, is referenced to, or merged to, or fit in the sense of optimal placement within other structures, such as points on the skin. An analogy may be drawn by use of the brain and fitting that into the skull, and the placement of other anatomical structures within the body itself, one relative to another, according to algorithms or generally known knowledge about such placements so as to register image data to physical data. It is an example of merging internal anatomical structures, points, or landmarks to other anatomical points or landmarks, each being in different coordinate spaces, such as the stereotactic coordinate space or physical coordinate space and the image coordinate space. Such referencing, therefore, may create a mapping, transformation, or correspondence between these coordinate spaces so as to thereafter position instruments or external apparatus relative to targets defined in the coordinate space to positions in the physical space or to determine targets or image positions in the image space from external apparatus or digital navigators that are known relative to the physical or stereotactic space.

In FIG. 18, the discrete dots such as 1036 may actually represent contours over the scalp, and in particular it may be over the indented scalp so as to reach the bone by a compressed scalp. This would give a good representation of the position of the skull based on indentation of the scalp, without breaking the scalp, so as to reach the bone. The cloud of physical points, therefore, such as points 1036 and 1032, do not correspond to a reference point, or fiducial point, or marker point on the skin of the patient, but rather a point which corresponds to a point within the body, or within the skin, or below the surface of the body in its natural shape, and in a shape which is visualized in traditional image scanning with the scalp that is not indented. Thus, the cloud of physical reference points, such as point 1036, represent physical positions that are within the normal state of the anatomical structure, i.e., inside the body and within the surface of the skin or the contours of the body.

The dashed line in FIG. 18 corresponds to a segmented representation of the outer table of the bone or some aspect of the bone, either the outer or the inner table, but the outer table would be convenient for this example. It may be reduced to a cloud of image data points, or it may be reduced to a series of contours of the bone, such as a spline representation or a triangular or geometric plate representation of the bone. The concept of matching such a dashed image related representation of the bone to a physically derived representation of the bone via the contact physical points or the depressed skin points 1036 may be done by a variety of either computer-theoretical or intuitive, graphical, and visualization methods. For example, the algorithm of Palazano and Chen shows how a least-square fit may be utilized to match two three-dimensional surfaces. In this case, the two surfaces might be the cloud of physical points 1036 and the cloud of image surface points represented by the surface. The matching may also be done by a chamfer algorithm, which basically indicates a minimization procedure on random sets of points in the cloud of surface points so as to minimize distances between or to minimize a point-to-point function between points. The distance, on the average, of the final "best fit" or optimal fit may simply be that the distance function is non-zero, indicating that there is a physical separation indicated by the compressed skin between the physical acquisition points such as 1036 and the bone which lies below it, 1030. Or, a scale factor may be used to upscale slightly the perimeter 1030 so as to have it fit optimally with zero on average distance function in a chamfer algorithm or a distance minimization sense to the cloud of points represented by the point 1036. A more graphical method may be also used wherein a three-dimensional representation 1030 of a surface appropriately tiled or splined may be looked at in different color, for example, from a tiled, or splined, or analytically continued surface of the physical points 1036. Such two surfaces may be independently translated or rotated in the linear and rotational degrees of freedom on a computer workstation, and the operator, with a joystick, may scale up the structures or leave them in their initial metric or distance scale factor and manipulate them so that they best overlap from a visual point of view. The visualization may be done in orthogonal cardinal plane slices or may be done in three dimensions looking at contour of the extreme projections of each of the physical and image contours. Any number of other qualitative, quantitative, graphical, or computer theoretical methods may be devised by those skilled in the art to make such a mapping with respect to the image-produced representation of the bone or other internal structures.

These examples illustrate how internal anatomical structures may be used to make such a transformation. The use of the skull is interesting because it is an invariant structure, which is very firm and stable. In contrast, the skin or scalp of a patient may be quite variable depending on his physical state, his disease, the way in which he is lying on the table, or other perturbations of the skin. Thus, indenting the scalp, as illustrated in FIG. 16, may represent a more faithful representation of the internal invariant structure represented by the skull. Thus, such a mapping, as illustrated by FIGS. 16, 17, and 18, is an interesting alternative method of doing the frameless transformation.

Another point in the application of referencing to the bony anatomy is the application to ear, nose, and throat (ENT) surgery. FIG. 16 shows points corresponding to skin indentation around the eyes, nose, and face, illustrated by points 1040, 1041, 1044, and 1046. If the bony anatomy, as segmented from image scanning, is fused to approximate points of physical registration using a probe such as 998A, then the exquisite and detailed characteristic features of the patient's face and bony skeletal around the eyes and nose may be fused in the image space to the physical space. This may be very helpful in ENT surgery where one intends to place a stereotactic probe, such as an instrument analogous to 998A, up through the nose into the sinuses, which are very close to the bony anatomy represented by points such as 1040. Thus, by registering the image space to the physical space by using such points and, in particular, referencing to the bony landmarks which are invariant to skin condition, then an interesting method for stereotactic registration and navigation may be applied in the sinuses and around the eyes. Thus this application is within the scope of the present patent application. Once the transformation between the image scan coordinate system and its related image scan data of the patient's anatomy is related to the coordinate system of a space probe, or equivalently the coordinate system of the detector for the space probe, then the position of the space probe or digitizer is known with respect to the image scan data of the patient's anatomy. Thus, as the space probe or navigator is moved in space near the physical patient's anatomy, its position may be related to the image scan data of the patient's anatomy, and therefore, its position may be displayed relative to the image scan data of said patient's anatomy. The image scan data of said patient's anatomy may be displayed in slices or three-dimensional volumetric views on a computer graphic workstation display, and the position of the space probe may be related to these views. For example, if the space probe has a tip, as in a surgical instrument or a focal point as in a microscope which is adapted to be detected as described in the parent application, the tip of the probe or the focus of the microscope may be displayed on slice data corresponding to the image scan data of the patient's anatomy. Moving the space probe, the microscope, or any other tool which is detected as a space probe by a detector system, one may call up the image slice or the volumetric view of the image scan data of the patient's anatomy corresponding to the tip at that instant of the space probe or the focal point, in the case of a microscope, relative to the patient's anatomy. All these manipulations which follow from the method and apparatus embodied in the parent application and this continuation-in-part are included within the scope of the invention.

FIG. 19A shows a device which, as an example, may be used to determine the physical measurement or representation of the internal anatomical structure, as indicated by the outer table of the skull or bone. In FIG. 19A, layer 1048A represents the bone; for example, in the head it would be the skull, and in other parts of the body it may be the ribs, the pelvis, or any other part of the body. Layer 1050A represents the scalp which will overlie the bone. A probe 1052A is used to press on the scalp and its tip 1054A indents the scalp, as shown, so that there is a closer approximation of the tip 1054A to the nearest point on the bony structure, which is represented by point 1056A on the bone, well within the body. Essentially, the probe 1052A carries index markers or spots 1058 and 1217A as for location sensing in accordance with the techniques described above. Also, a calibration structure 1230A may comprise a part of the probe 1052A including a slider 1231A and a scale 1232A. The structure of FIG. 19A illustrates how internal anatomical structures may be used to make transformations. The use of the skull is interesting because it is an invariant structure which is very firm and stable. In contrast, the skin or scalp of a patient may be quite variable depending on his physical state, his disease, the way in which he is lying on the table, or other perturbations of the skin. Thus, indenting the scalp, as illustrated in FIG. 19A, may represent a more faithful representation of the internal invariant structure represented by the skull. Thus, such a mapping, as illustrated by FIGS. 16, 17, and 18, is an interesting alternative method of doing the frameless transformation.

FIG. 19B shows another embodiment of the invention which may also detect the position of the bony anatomy and determine the coordinates of physical points on the bony anatomy. A probe 1052A has a multiplicity or array of optically detected devices 1058B and is pressed against the skin 1050B which overlies the skull or a bony structure 1048B. The front end of the probe 1060B may or may not indent the scalp. Inside the probe 1052B there is an ultrasonic sender which emits ultrasonic waves 1062B which may reflect off the bony surface or point of the bony surface beneath the probe indicated by 1056B and thereby determine the position of the bony point 1056B relative to the probe 1052B, and therefore relative to the digitizing tracking means 1058B. Digital detector means such as 1064B and 1066B are observing or detecting the position of the probe 1052B, and therefore may detect the position of the bony point 1056B directly. The ultrasonic probe has associated electronics or power means 1068B, which powers it, may send out the ultransonic signal, may receive the reflected ultransonic signal and determine a time delay between sending and receiving so as to determine the distance, for example T2, between the end of the probe 1060B and the reflecting bony object 1056B. This method of ultrasonic distance detection is commonly known in the prior art and does not need to be described further here. The use of ultrasonic distance detection methods in the body is well known, and typically relies on time-of-flight determination of ultrasonic signals which are reflected off sonogenic or highly reflective structures such as bone within the body. The information from the stereotactic digitizing probe 1052B, which might be achieved by the detectors 1064B and 1066B may be fed to the stereotactic space probe data processing unit or devices 1070B, and this may be used in conjunction with the ultrasonic distance detector 1068B, as indicated by the line connecting these two objects in FIG. 19B, to provide the coordinate information for an internal or bodily reference point such as 1056B. The coordinates of 1056B may therefore be determined in the coordinate space of the detectors, such as 1064B and accumulated in the computer 1072B for fusion and coordinate transformation with image data which may have been accumulated by an image scanner and processing unit 1074B. The skull, for example, may have been determined from image scan data, CT, MRI, angiography, or other means beforehand and, as described above, this image data may be manipulated in three dimensions to give a computer graphic rendering of the skull of the patient. That rendering may thereafter be fused or mapped to the coordinate points as determined by the probe device such as 1052B in FIG. 19B, and thereby the coordinate transformation between the physical coordinate space of the detectors and the probe, and the coordinate space of the image scan may be made. Thus, FIG. 19B illustrates one of a number of embodiments which may be used to determine or detect internal structures or points and correlate them to image scan data corresponding to those reconstructed points or structures or analogous structures.

It is noted that the physical, mechanical, or electrical technique or principle upon which the space digitizer operates in the above examples may vary significantly. Examples here are given of optical cameras and tracking with LEDs or reflectors. Machine vision is also possible which has to do with pattern recognition of objects visualized in cameras. In relation to certain embodiments, articulated mechanical arms, electromagnetic means, ultrasonic means, or other means of digitization may also be used. Internal structures other than the skull may be used; other bony anatomy may be used; internal objects such as the liver, parts of the brain, or other detectable portions of the anatomy, internal or on the surface of the body, may be used for this purpose. A variety of means of detecting the internal structures such as X-ray detection by fluoroscopy or orthogonal X-ray machines or single X-ray machines may be used to determine the internal structures and their coordinates relative to the physical space. Use of X-ray machines or local MRI detectors or local ultrasonic detectors may similarly be used. Hand-held ultrasonic scanners may be used to coordinate the coordinate space of an ultrasonic scanner with the physical position of the scanner handle so as to relate the position of an internal structure detected by the ultrasonic scan image to the position of the ultrasonic handle, and this correlated to image scan data taken by another scanning means to correlate the physical space to the image scan space. Use of internal markers that are placed within the bone or other anatomy that are subsequently detected by X-ray means or ultrasonic means or electromagnetic detection means may be similarly used as internal natural or man-made reference markers or implanted reference markers so as to map the physical space of the anatomy to the coordinate space of the image scan data. For example, a hand-held X-ray machine or a hand-held ultrasonic scanner may be used to give a two-dimensional representation of the body with respect to that X-ray machine or ultrasonic image scanner. This quantitative data relative to the image scanner may then be used to map to the coordinate space of camera detectors or other navigation or mechanical digitization detection means associated with other external apparatus or external apparatus related to the X-ray or ultrasonic machine near the patient's body. Such data may be coordinated within the computer workstation and then the representation of the body may be mapped into a coordinate space related to the external apparatus, and thus to the external environment relative to the patient. For example, the ultrasonic detector handle 1052B, which is shown in FIG. 19B, rather than being just a distance measuring device may be an actual ultrasonic scanner. This may be indicated by the dashed lines 1076B, which then represent the scan space of the ultrasonic imaging device, either in a one-dimensional plane or possibly in a multi-dimensional plane. Such an ultrasonic scan fan is common in the diagnostic ultrasonic detection technology now used in clinical application. It may be used to detect an object 1078B, which is internal to the patient's body, and determine the physical coordinates of that object 1078B relative to the ultrasonic head 1052B, and therefore to the external detection system 1064B and 1066B. This, in turn, as indicated by the block diagram, may be coordinated in the space of the probe data 1070B, and therefore correlated or fused by the element 1072B with image data 1074B taken by another imaging means. The correlation of the physical object coordinate data and the image scan coordinate data may be rendered and represented on a computer graphic screen 1080B, and the fusion may be done by the operator by manipulating the image scan versus the physical scan objects on that graphics display 1080B. Shown on the graphics display in FIG. 19B are dashed curves, for example, which might represent the image scan data representation, and solid curves which may represent the physical coordinate representation of the physical objects. They may be transformed, rotated, translated in standard orthogonal coordinate planes or other physical coordinate planes so as to overlap and merge them. At the same time, the position of the probe detector 1052B may be shown relative to these anatomical structures on the computer graphic screen 1080B and the entire picture coordinated as would be done to pre-plan or perform intervention clinically into the patient's body.

FIGS. 20A and 20B illustrate an alternative anatomy in relation to the system of the present invention. In that regard, a vertebral structure 2002 is shown as part of a patient's anatomy, along with an index plate 2030 and a probe or rod 2005. In accordance herewith, the vertebral structure 2002 is scanned to provide three dimensional data as described above. Real time data, relating to the configuration in position of the vertebral structure 2002 and the position of the rod 2005 and the plate 2030 is then correlated with the stored data to accomplish effective and useful displays in accordance herewith.

Generally, the rod 2005 carries source LED lights 2006 and 2007 for camera tracking as explained above. Somewhat similarly, the plate 2030 (affixed to the structure 2002 by a screw 2034) also carries light source LED's 2031, 2032 and 2033 for real time tracking. Accordingly, of the vertebral structure 2002, a vertebral bone 2012 may be depicted as the bone image 2012A (FIG. 20B).

Considering FIGS. 20A and 20B in somewhat greater detail, a surgical incision 2001 is depicted in a patient's back exposing the vertebral structure 2002 with its spinous process 2008, projecting posteriorly. The adjoining vertebral structure 2003 (below) and 2004 (above) are also illustrated.

A surgery may involve removal of bone to approach the intervertebral disc or nerves. Also, pedicel screws may be inserted from one vertebral structure to another fixing vertebrae together. In relation to the system hereof, upon exposing the specific vertebrae 2002, the rod 2005 can be moved to "swab" or sense position points to define the external configuration. In that regard, the complex surface of the vertebrae bone 2002 can be mapped. Accordingly, the sensed data, provided from the index sources on the plate 2030 and the rod 2005 may be processed to define, store and display the image 2012A (FIG. 20B). Accordingly, the vertebral structure 2002 can be viewed independently. Also, the structure can be segmented or isolated as by graphic software using the scan data, e.g. CT or MR data.

As another embodiment of the present invention, FIG. 21 shows the tracking of the patient's anatomy as described above, with an instrument, and also the tracking of the surgeon's head. Head lamps or head loops are attached to the patient's head. In FIG. 21, the cameras 2111 and 2112 are attached to a stationary bar 2114. A signal coupler 2115 provides the signals to 2121 through a processor which integrates stored data in storage means 2123 from image scanner 2124. Image scan data or image slices in three-dimensional reconstructions are shown on the computer workstation 2122, as discussed above.

The patient's anatomy has a clamp 2102 attached by screws 2103 to the patient's head 2101. Index lights, for example 2108, enable tracking of the head clamp by the cameras. Alternatively, a geometrically triangular plate such as 2110 with index points or LED's 2109, etc. could also track dynamic movement of the patient's head. An instrument placed through surgical opening 2104 also has LED's 2106 and 2107 viewed by the cameras so as to determine, via the computer system 2122, the position of the surgical tip or target, for example 2105 relative to the stereotactic space and the image slice data of the CT or MRI scans. The surgeon 2130 is viewing the field, and has attached a head strap 2131 which may also include LED's or other index means such as 2132, etc. In addition, there may be surgical magnifiers, lenses, cameras, glasses, loops or lights such as 2134 and 2135, through which the surgeon is looking at the surgical field. Thus in this situation, not only are the instruments, microscope, and/or tools being tracked by the camera system, but also the surgeon himself or the eye pieces that he wears, and thus his view of the surgical field, through, for example, the surgical eye pieces or loops. In this case it is shown that the surgeon or equipment which the surgeon carries is part of the digitized and tracked objects in the digitizing field.

Figure 22:
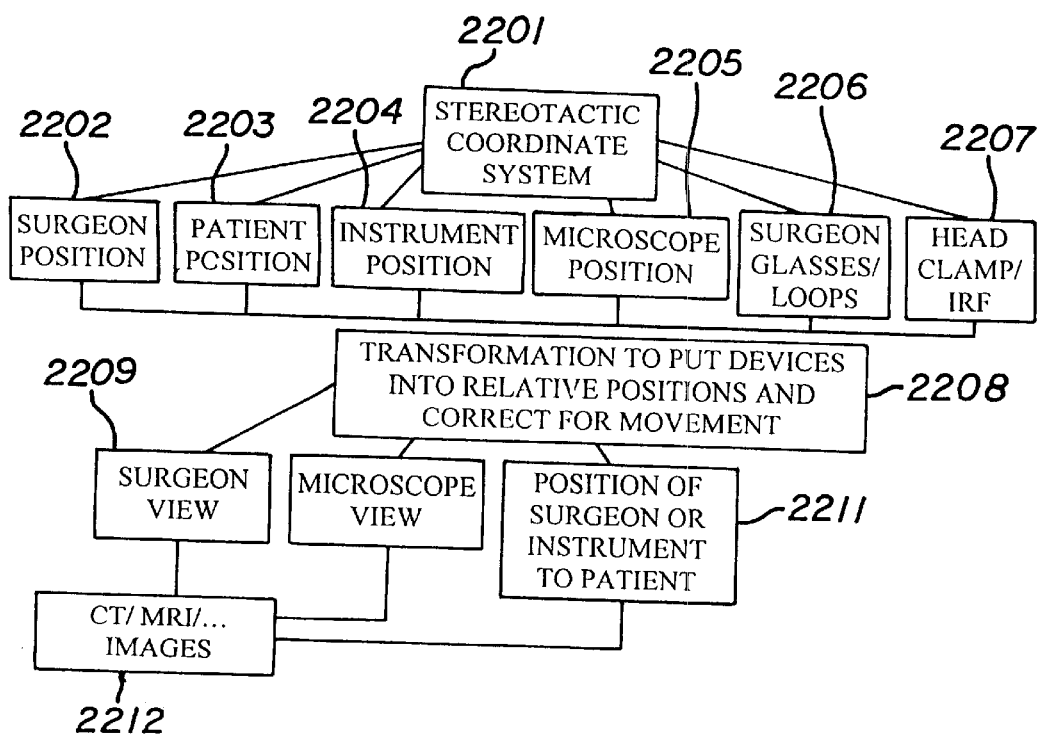
FIG. 22 is a block diagram illustrating another aspect of a system with relative coordinate referencing of multiple objects including a surgeon, patient, instruments, microscope, etc. with respect to each other and to CT, MRI, or other image data.

FIG. 22 summarizes again a flow diagram of some of the objects in this invention. CT and MR images can be stored in computer 2212 or other processing means. The stereotactic coordinate system of the cameras or other digitizer 2201 provides coordinates of the various objects in the field, including the surgeon's position 2202 via surgeon tracking means such as in FIG. 21; patient position 2203, which may have to do with LED's or other markers placed on the patient's skin or on associated clamps; instrument positions 2204, as described above; a microscope position 2205, also described above; surgeon's glasses or loops, as described in FIG. 21; and a head clamp 2207, which might be clamped to the patient's head or the surgeon's head and corresponds to a dynamic reference frame so as to integrate, compare, and correct for relative motions of all of these objects in real time. The positions of these objects can be transformed by mathematical transformations, such as referenced above, by element 2208 so as to correct for their relative positions or put their positions all into the stereotactic coordinate system of the digitizer 2201. Once this transformation has been done, then the surgeon view 2209 through the surgical loops, or the microscope view 2210, or the position of any of the objects or persons, patient, or surgeon 2211 can be integrated and registered in the computer 2212 so that image scan data from the CT scanners can be reconstructed and displayed in the views of the surgical loops or surgeon microscope or any other view and correlated to the actual scene as viewed by the surgeon correspondingly.

Figure 23:
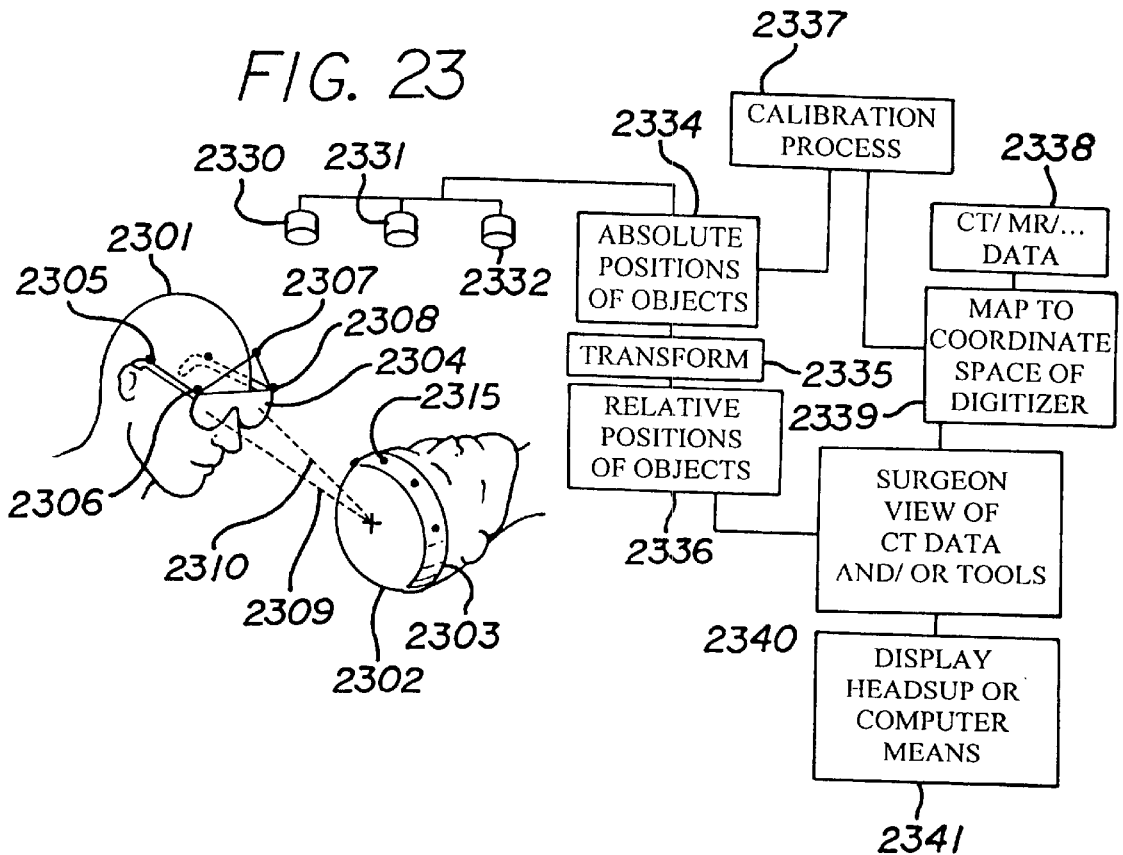
FIG. 23 is a perspective view of a system illustrating the use of the transformation process to supply coordinate transformations for heads-up display or surgeon view reconstructions from image scan data.

FIG. 23 shows another variant of this where the patient 2302 and the surgeon 2301 have positions which are being tracked by the cameras 2330, 2331, and 2332. In this case, surgical glasses 2304 with index or tracking LED's 2308, 2307, 2306, and 2305 track the position of the surgeon's head and his view. The orientation of his view to the patient, indicated by dashed lines 2310 and 2309 in stereoscopic or stereotactic view, can now be known relative to the patient's anatomy by the calibration process and relative transformation described above. For example, the camera data of the digitizer provides absolute positions relative to the digitizer 2334 via a calibration process 2337. These can then be transformed by transform 2335 to relative positions 2336 of the objects. Thus, the surgeon's view can be mapped to the view corresponding to CT data 2340 which corresponds to the mapping of image data from a CT or MR scanner 2338 via a coordinate transformation device 2339. In this way, the view in the image scan data of the surgeon's view 2310 and 2309 can be simulated and displayed on display elements 2340 and transported into the goggles 2304 in the form of a "heads up display" such as fighter pilots use in modern jet aircraft. Also shown in FIG. 23 are index or tracking points 2315, etc. on the patient to track his or her position. Thus, the glasses 2304 can have small cameras or fiber optic carriers which can bring in images from the assimilated image data 2340 and 2341 so that the surgeon may see in the upper corner of his or her glasses the picture of the reconstructed image scan data as reconstructed in the direction of his or her physical view 2310 and 2309. Thus, a superposition of the image scan data with the actual view can be done within the surgeon's glasses as he or she moves his or her head relative to the patient, all of this being updated and dynamically referenced to the patient.

Figure 24:
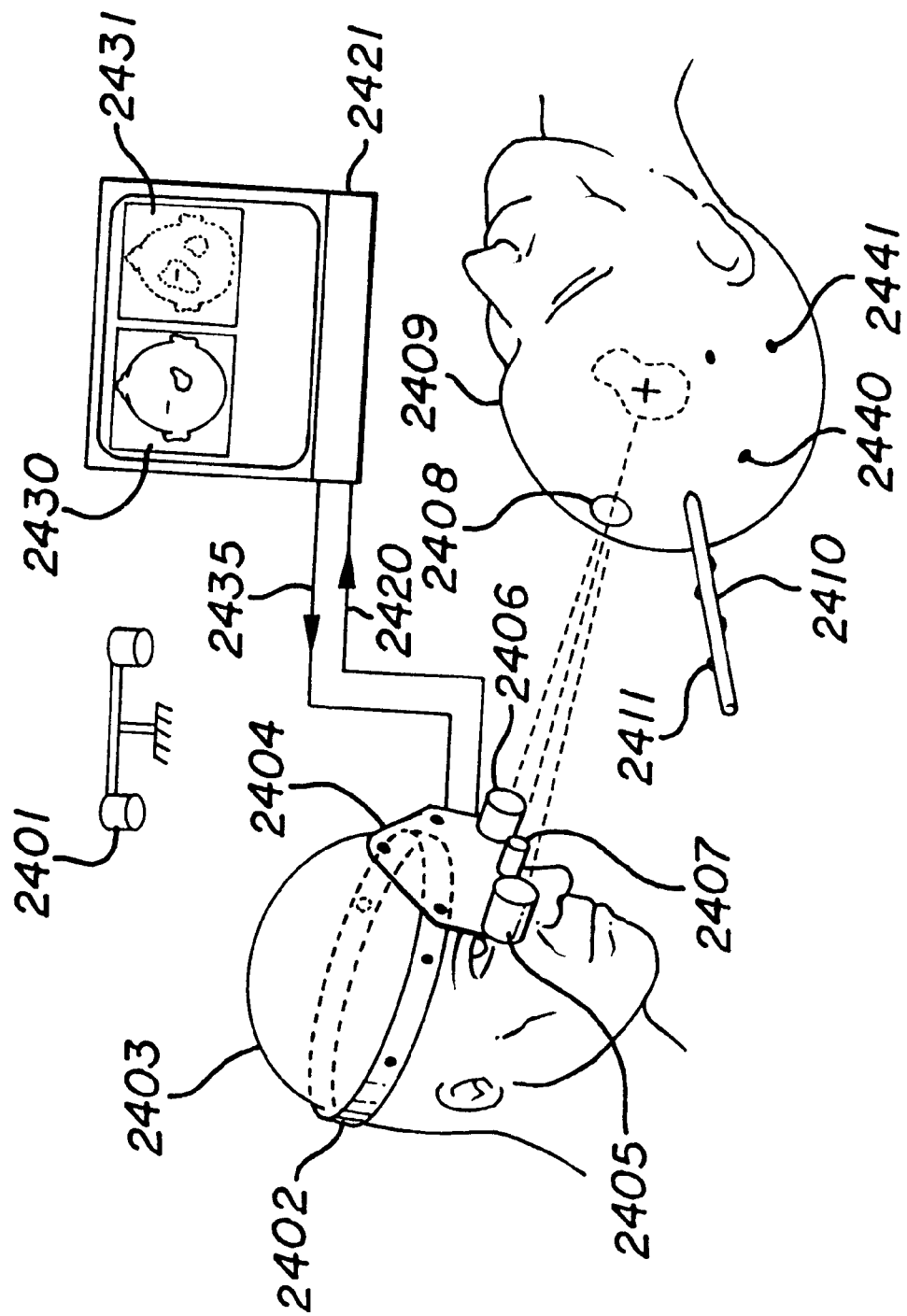
FIG. 24 is another perspective view relating to the use of a heads-up display, goggles, or surgical loops that are being tracked by a digitizer relative to a patient's anatomy so as to compare an actual view to a reconstructed view from a surgeon's perspective.

FIG. 24 shows a similar situation where cameras 2401 track a head band 2402 on the surgeon's head 2403. LED'S such as 2404 (and others unmarked) track the surgeon's head and also track the orientation of optical viewers 2405 and 2406, such as optical loops which the surgeon is wearing. The surgeon can also be wearing a small camera 2407 which looks into the surgical opening 2408 in the patient's head 2409. A surgical probe 2410 with LED sensors such as 2411 may be in the surgical field. Data from the camera 2407 can be transferred via line 2420 to a computer 2421 and both views can be viewed on the screen. For example, on the screen in view 2430 is the actual view as seen by the camera 2407 along the viewing path 2432. Also shown on the screen is reconstructed view 2431 corresponding to reconstructed image scan data (CT, MR, etc.) along that same path and reconstructed at various depths along that path. Such reconstructed image data can be piped by an optical line or electronic line 2435 back to the surgeon's goggles 2405 and 2406 and can be piped into the field of view as with a heads-up display or by a split mirror and camera system within the goggles. In this way the surgeon can actually visualize the graphic rendered reconstructed view as he looks towards the patient, that graphics view being reconstructed in the same direction the surgeon is viewed to the patient. Reference markers or dynamic reference points 2440, 2441, and others might be attached to the patient or to a clamp attached to the patient or to some other head band or other means on the patient so as to track the relative position of the actual patient anatomy to the surgeon's field of view as well as the views through his optical loops such as 2405 and 2406.

Having described the exemplary methods and structures, what is claimed is:

1. A system using designated index locations, for indicating positional relationships of an object field including a surgical instrument as related to a subject patient's anatomy represented by image-scanner data, said system comprising:

a memory for storing said image-scanner data representing the subject patient's anatomy and referenced in scanner-data coordinates to said designated index locations;

a camera apparatus for providing position data indicative of said designated index locations and said surgical instrument whereby to track said surgical instrument in relation to said designated index locations;

a computer graphics apparatus for transforming at least one of said position data and said image-scanner data to provide said image-scanner data and said position data in compatible coordinates;

an image generator for combining said image-scanner data and said position data to form combined display data; and a display unit for receiving said combined display data to provide an image display including the subject patient's anatomy.

2. A system according to claim 1 further including index means to indicate said designated index locations, said index means adapted to be affixed to the subject patient's anatomy.

3. A system according to claim 2 wherein said index means comprises a light source.

4. A system according to claim 3 wherein said light source comprises a diode.

5. A system according to claim 3 wherein said light source comprises a reflector.

6. A system according to claim 2 wherein said index means comprise geometric means.

7. A system according to claim 6 wherein said geometric means comprises a triangular plate.

8. A system according to claim 1 further including an array projector for projecting an optically detectable array of light points on the subject patient's anatomy to indicate said designated index locations.

9. A system according to claim 8 wherein said array projector comprises a laser grid generator.

10. A system according to claim 1 further including a mechanical holder adapted to be affixed to said subject patient's anatomy and holder index means detectable by said camera apparatus to provide reference data for referencing said subject patient's anatomy to preserve said display data with positional changes of said subject patient's anatomy.

11. A system according to claim 1 wherein said computer graphics apparatus computes at least one pattern recognition transformation to determine, from said position data, a pattern of said surgical instrument.

12. A system according to claim 1 wherein said camera apparatus comprises at least one CCD camera.

13. A system according to claim 1 wherein said camera apparatus comprises at least one video camera.

14. A system according to claim 1 wherein said surgical instrument comprises a microscope.

15. A system according to claim 14 wherein said microscope includes a plurality of optically detectable objects detectable by said camera apparatus to provide said location data.

16. A system according to claim 1 wherein said system further includes a scanner for scanning the subject patient's anatomy to provide said image-scanner data.

17. A system according to claim 1 further including index means adapted to be affixed to said patient's anatomy to indicate said designated index locations.

18. A system according to claim 1 wherein said designated index locations comprise natural anatomical landmarks.

19. A system according to claim 1 further including an optically detectable probe, whereby said camera apparatus senses said optical probe to determine locations of said designated index locations in said object fields.

20. A system according to claim 1 wherein said surgical instrument comprises at least one marker detectable by said camera apparatus for providing a representation of said surgical instrument in said image display.

21. A system according to claim 1 wherein said surgical instrument comprises at least one light source detectable by said camera apparatus for providing a representation of said surgical instrument in said image display.

22. A system according to claim 1 wherein said surgical instrument comprises at least one reflector detectable by said camera apparatus for providing a representation of said surgical instrument in said image display.

23. A system according to claim 22 further including at least one light source for projecting light onto said at least one reflector.

24. A system according to claim 1 further including at least one marker adapted to be affixed to said subject patient's anatomy to indicate at least a portion of said designated index locations.

25. A system according to claim 24 wherein said surgical instrument comprises at least one light source.

26. A system according to claim 25 wherein said at least one light source comprises a light emitting diode.

27. A system according to claim 25 wherein said at least one light source comprises a reflector.

28. A system according to claim 24 wherein said at least one marker comprises at least one light source.

29. A system according to claim 28 wherein said at least one light source comprises at least one reflector.

30. A system according to claim 28 wherein said at least one light source comprises at least one diode.

31. A system according to claim 1 further including a mechanical holder adapted to be affixed to said subject patient's anatomy, said holder comprising at least one light source detectable by said camera apparatus to provide reference data for referencing said subject patient's anatomy.

32. A system according to claim 1 further including a mechanical holder adapted to be affixed to said subject patient's anatomy, said holder comprising at least one reflector detectable by said camera apparatus to provide reference data for referencing said subject patient's anatomy.

33. A method of determining the positional relationship of a surgical instrument with respect to a subject patient's anatomy comprising the steps of:

designating at least one index location for detection in relation to the subject patient's anatomy and the surgical instrument;

storing three dimensional image scanner data representative of the subject patient's anatomy in scanner-data coordinates and referenced to said at least one index location;

determining, using a camera system, the position of said surgical instrument in detector coordinates relative to the subject patient's anatomy based on said at least one index location and represented by surgical instrument data;

correlating the surgical instrument data and the image scanner data representative of the subject patient's anatomy to a compatible coordinate system;

combining said surgical instrument data and said image scanner data in said compatible coordinate system to provide display signals; and driving a computer graphics display with said display signals to display said surgical instrument in relation to said subject patient's anatomy.

34. A method according to claim 33 further including the step of affixing at least one index marker to said subject patient's anatomy to indicate said index locations.

35. A method according to claim 34 wherein said at least one index marker comprises at least one radiopaque marker.

36. A method according to claim 34 wherein said at least one index marker comprises at least one light source.

37. A method according to claim 36 wherein said at least one light source comprises at least one diode.

38. A method according to claim 36 wherein said at least one light source comprises at least one reflector.

39. A method according to claim 34 further including the step of detecting light from at least one light emitting diode on said surgical instrument.

40. A method according to claim 34 further including the step of detecting light from at least one reflector on said surgical instrument.

41. A method according to claim 40 further including the step of projecting light onto said at least one reflector to track said surgical instrument.

42. A method according to claim 33 wherein said at least one index location comprises at least one natural anatomical landmark.

43. A method according to claim 33 further including the step of projecting an optically detectable array of light points on said subject patient's anatomy to indicate said at least one index location.

44. A method according to claim 33 further including the step of affixing a mechanical holder to said subject patient's anatomy, said mechanical holder comprising holder index means detectable by said camera system to provide reference data for referencing said subject patient's anatomy to preserve said display signals with positional changes of said subject patient's anatomy.

45. A method according to claim 33 further including the step of affixing a mechanical holder to said subject patient's anatomy, said mechanical holder comprising at least one reflector detectable by said camera system to provide reference data for referencing said subject patient's anatomy.

46. A method according to claim 33 further including the step of affixing a mechanical holder to said subject patient's anatomy, said mechanical holder comprising at least one light source detectable by said camera system to provide reference data for referencing said subject patient's anatomy.

47. A method according to claim 33 further including the step of computing at least one pattern recognition transformation to determine, from said surgical instrument data, a pattern of said surgical instrument.

48. A method according to claim 33 wherein said surgical instrument comprises a microscope including a plurality of optically detectable objects, the method further including the step of detecting said optically detectable objects by said camera system to provide at least a portion of said surgical instrument data.

49. A method according to claim 33 further including the step of scanning said subject patient's anatomy to provide said image scanner data.

50. A method according to claim 33 further including the step of detecting at least one marker on said surgical instrument.

51. A method according to claim 33 further including the step of detecting at least one light source on said surgical instrument.

52. A method according to claim 33 further including the step of detecting at least one reflector on said surgical instrument.

53. A method according to claim 52 further including the step of projecting light onto said at least one reflector to track said surgical instrument.

54. A method according to claim 33 further including the step of sensing an optically detectable probe to designate said at least one index location.

55. A system using designated index locations, for indicating positional relationships of an object field including a surgical instrument as related to a subject patient's anatomy represented by image-scanner data, said system comprising;
 a memory for storing said image-scanner data representing the subject patient's anatomy and referenced in scanner-data coordinates to said designated index locations;
 a camera apparatus for optically sensing said object field from plural different fields of view to provide location data comprising first data associated with said designated index locations and second data associated with said surgical instrument;
 a computer graphics apparatus for transforming at least one of sad location data and said image-scanner data to provide said image-scanner data and said location data in compatible coordinates;
 an image generator for combining said image-scanner data and said location data to form combined display data; and
 a display unit for receiving said combined display data to provide an image display including the subject patient's anatomy.

56. A system according to claim 55 wherein said surgical instrument comprises at least one light source detectable by said camera apparatus.

57. A system according to claim 55 wherein said surgical instrument comprises at least one reflector detectable by said camera apparatus.

58. A system according to claim 55 further including at least one marker adapted to be affixed to said subject patient's anatomy to indicate at least a portion of said designated index locations.

59. A system according to claim 58 wherein said surgical instrument comprises at least one light source.

60. A system according to claim 59 wherein said at least one light source comprises a light emitting diode.

61. A system according to claim 59 wherein said at least one light source comprises a reflector.

62. A system according to claim 58 wherein said at least one marker comprises at least one light source.

63. A system according to claim 62 wherein said at least one light source comprises at least one reflector.

64. A system according to claim 62 wherein said at least one light source comprises at least one diode.

65. A system according to claim 55 further including a mechanical holder adapted to be affixed to said subject patient's anatomy, said holder comprising at least one light source detectable by said camera apparatus to provide reference data for referencing said subject patient's anatomy.

66. A system according to claim 55 further including a mechanical holder adapted to be affixed to said subject patient's anatomy, said holder comprising at least one reflector detectable by said camera apparatus to provide reference data for referencing said subject patient's anatomy.

67. A system using designated index locations, for indicating positional relationships of an object field including a surgical instrument as related to a subject patient's anatomy represented by image-scanner data, said system comprising:
 a memory for storing said image-scanner data representing the subject patient's anatomy and referenced in scanner-data coordinates to said designated index locations;
 a camera apparatus for sensing plural fields of view of said object field for tracking said surgical instrument in said fields of view relative to said designated index locations, said camera apparatus providing location data relating said surgical instrument to said image scanner data;
 a computer graphics apparatus for transforming data based on said index locations to provide said image-scanner data and said location data in compatible coordinates;

an image generator for combining said image-scanner data and said location data to form combined display data; and a display unit for receiving said combined display data to provide an image display including the subject patient's anatomy.

68. A system according to claim 67 wherein said surgical instrument comprises at least one light source detectable by said camera apparatus.

69. A system according to claim 67 wherein said surgical instrument comprises at least one reflector detectable by said camera apparatus.

70. A system according to claim 67 further including at least one marker adapted to be affixed to said subject patient's anatomy to indicate at least one of said designated index locations.

71. A system according to claim 70 wherein said surgical instrument comprises at least one light source.

72. A system according to claim 71 wherein said at least one light source comprises at least one light emitting diode.

73. A system according to claim 71 wherein said at least one light source comprises at least one reflector.

74. A system according to claim 72 wherein said at least one marker comprises at least one light source.

75. A system according to claim 74 wherein said at least one light source comprises at least one reflector.

76. A system according to claim 74 wherein said at least one light source comprises at least one diode.

77. A system according to claim 67 further including a mechanical holder adapted to be affixed to said subject patient's anatomy, said holder comprising at least one light source detectable by said camera apparatus to provide reference data for referencing said subject patient's anatomy.

78. A system according to claim 67 further including a mechanical holder adapted to be affixed to said subject patient's anatomy, said holder comprising at least one reflector detectable by said camera apparatus to provide reference data for referencing said subject patient's anatomy.

79. A system according to claim 17 wherein said index means comprise radiopaque markers.

* * * * *